United States Patent
Cha et al.

(10) Patent No.: US 10,991,886 B2
(45) Date of Patent: Apr. 27, 2021

(54) AMINE-BASED COMPOUND AND ORGANIC LIGHT EMITTING DEVICE COMPRISING SAME

(71) Applicant: LG Chem, Ltd., Seoul (KR)

(72) Inventors: Yongbum Cha, Daejeon (KR); Sung Kil Hong, Daejeon (KR); Jin Joo Kim, Daejeon (KR)

(73) Assignee: LG Chem, Ltd.

( * ) Notice: Subject to any disclaimer, the term of this patent is extended or adjusted under 35 U.S.C. 154(b) by 219 days.

(21) Appl. No.: 15/757,470

(22) PCT Filed: Sep. 2, 2016

(86) PCT No.: PCT/KR2016/009852
§ 371 (c)(1),
(2) Date: Mar. 5, 2018

(87) PCT Pub. No.: WO2017/039388
PCT Pub. Date: Mar. 9, 2017

(65) Prior Publication Data
US 2018/0248119 A1    Aug. 30, 2018

(30) Foreign Application Priority Data

Sep. 4, 2015  (KR) .......................... 10-2015-0125525

(51) Int. Cl.
*H01L 51/00*    (2006.01)
*C07C 211/61*   (2006.01)
(Continued)

(52) U.S. Cl.
CPC .......... *H01L 51/006* (2013.01); *C07B 59/001* (2013.01); *C07C 13/72* (2013.01); *C07C 15/38* (2013.01); *C07C 211/61* (2013.01); *C07C 255/58* (2013.01); *C07F 7/081* (2013.01); *C09K 11/06* (2013.01); *H01L 51/0094* (2013.01); *H01L 51/50* (2013.01); *C07B 2200/05* (2013.01); *C07C 2603/42* (2017.05); *C07C 2603/86* (2017.05); *C07C 2603/94* (2017.05);
(Continued)

(58) Field of Classification Search
None
See application file for complete search history.

(56) References Cited

U.S. PATENT DOCUMENTS 10,243,148 B2    3/2019   Kato et al.
2009/0134781 A1  5/2009   Jang et al.
(Continued)

FOREIGN PATENT DOCUMENTS

CN    104557440 A    4/2015
EP    2175005 A1     4/2010
(Continued)

OTHER PUBLICATIONS

Extended European Search Report including Written Opinion for Application No. EP16842354.9 dated Jul. 3, 2018.
(Continued)

*Primary Examiner* — Jay Yang
(74) *Attorney, Agent, or Firm* — Lerner, David, Littenberg, Krumholz & Mentlik, LLP

(57) ABSTRACT

The present specification provides an amine-based compound and an organic light emitting device including the same.

14 Claims, 1 Drawing Sheet

(51) Int. Cl.
     *C09K 11/06*     (2006.01)
     *C07F 7/08*     (2006.01)
     *H01L 51/50*     (2006.01)
     *C07C 15/38*     (2006.01)
     *C07C 13/72*     (2006.01)
     *C07C 255/58*     (2006.01)
     *C07B 59/00*     (2006.01)

(52) U.S. Cl.
     CPC .. *C07C 2603/97* (2017.05); *C09K 2211/1011* (2013.01); *C09K 2211/1014* (2013.01); *H01L 51/0054* (2013.01); *H01L 51/0056* (2013.01); *H01L 51/0058* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

2010/0108997 A1   5/2010   Kim et al.
2013/0153878 A1*  6/2013   Mizuki ................ C07D 307/91
                                                                       257/40
2017/0229649 A1   8/2017   Kato et al.

FOREIGN PATENT DOCUMENTS

| | | |
|---|---|---|
| JP | 2009530371 A | 8/2009 |
| JP | 2010132638 A | 6/2010 |
| JP | 2015009076 A | 1/2015 |
| JP | 2017001979 A | 1/2017 |
| KR | 20000051826 A | 8/2000 |
| KR | 20070096917 A | 10/2007 |
| KR | 20100041043 A | 4/2010 |
| KR | 20130125575 A | 11/2013 |
| KR | 20150010016 A | 1/2015 |
| KR | 20150012488 A | 2/2015 |
| KR | 20180015604 A | 2/2018 |
| WO | 2015009076 A1 | 1/2015 |
| WO | 2015012618 A1 | 1/2015 |
| WO | 2016013867 A1 | 1/2016 |
| WO | 2016199784 A1 | 12/2016 |

OTHER PUBLICATIONS

Search report from International Application No. PCT/KR2016/009852, dated Dec. 13, 2016.

* cited by examiner

[Figure 1]
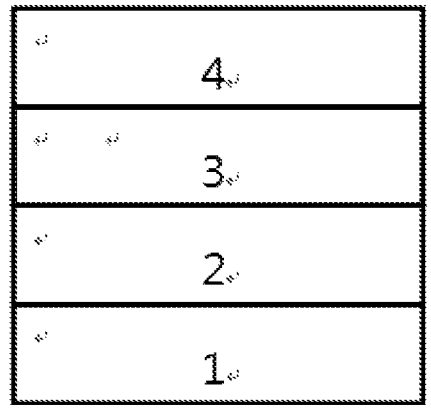
[Figure 2]
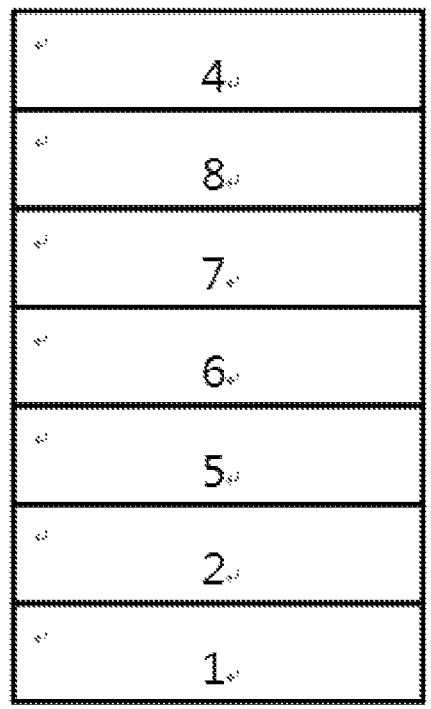

AMINE-BASED COMPOUND AND ORGANIC LIGHT EMITTING DEVICE COMPRISING SAME

CROSS-REFERENCE TO RELATED APPLICATIONS

The present application is a national phase entry under 35 U.S.C. § 371 of International Application No. PCT/KR2016/009852 filed on Sep. 2, 2016, which claims priority from Korean Patent Application No. 10-2015-0125525 filed in the Korean Intellectual Property Office on Sep. 4, 2015, the entire contents of which are incorporated herein by reference.

TECHNICAL FIELD

The present specification relates to an amine-based compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Official Gazette of Korean Patent Application Laid-Open No. 2000-0051826

DETAILED DESCRIPTION OF THE INVENTION

Technical Problem

The present specification describes an amine-based compound and an organic light emitting device including the same.

Technical Solution

An exemplary embodiment of the present specification provides a compound represented by the following Chemical Formula 1:

[Chemical Formula 1]

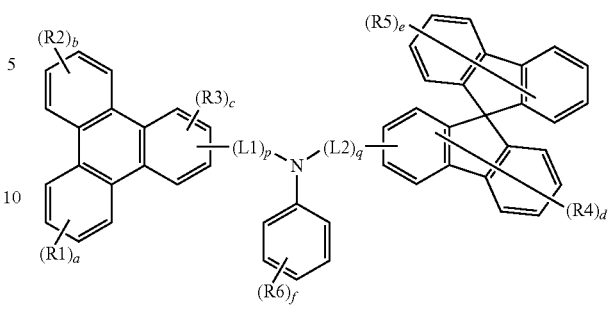

In Chemical Formula 1,

L1 to L2 are the same as or different from each other, and are each independently a direct bond; or a substituted or unsubstituted arylene, R1 to R3 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; or a substituted or unsubstituted heterocyclic group, or combine with an adjacent group to form a substituted or unsubstituted ring, R4 and R5 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a substituted or unsubstituted ring, R6's are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a substituted or unsubstituted ring, a and b are the same as or different from each other, and are each independently an integer of 0 to 4, c is an integer of 0 to 3, d is an integer of 0 to 7, e is an integer of 0 to 8, f is an integer of 0 to 5, p and q are the same as or different from each other, and are each independently an integer of 0 to 10, and when a, b, c, d, e, f, p, and q are each 2 or more, structures in the parenthesis are the same as or different from each other.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

Advantageous Effects

The compound described in the present specification may be used as a material for an organic material layer of an organic light emitting device. The compound according to at least one exemplary embodiment may improve the efficiency, achieve low driving voltage and/or improve lifetime characteristics in the organic light emitting device. In particular, the compound described in the present specification may be used as a material for hole injection, hole transport, hole injection and hole transport, light emission, electron transport, or electron injection. In addition, the compound described in the present specification may be preferably used as a material for a light emitting layer, and electron transport or electron injection. Furthermore, more preferably, according to an exemplary embodiment of the present specification, the compound may be used as a material for a hole injection layer, a hole transport layer, or an electron blocking layer.

DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transport layer 6, a light emitting layer 7, an electron transport layer 8, and a negative electrode 4.

MODE FOR INVENTION

Hereinafter, the present specification will be described in more detail.

In the present specification,  means a bond which is linked to another substituent.

An exemplary embodiment of the present specification provides the compound represented by Chemical Formula 1. Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

According to an exemplary embodiment of the present specification, the term "substituted or unsubstituted" may preferably mean being unsubstituted or substituted with one or more substituents selected from the group consisting of deuterium, a halogen group, a nitrile group, an alkyl group having 1 to 5 carbon atoms, an aryl group having 6 to 30 carbon atoms, and a heterocyclic group having 2 to 30 carbon atoms.

According to an exemplary embodiment of the present specification, the term "substituted or unsubstituted" may preferably mean being unsubstituted or substituted with one or more substituents selected from the group consisting of deuterium, a halogen group, a nitrile group, an alkyl group, a trimethylsilyl group, an aryl group, and a heterocyclic group.

According to an exemplary embodiment of the present specification, the term "substituted or unsubstituted" may preferably mean being unsubstituted or substituted with one or more substituents selected from the group consisting of deuterium, a halogen group, a nitrile group, an alkyl group having 1 to 5 carbon atoms, a trimethylsilyl group, an aryl group having 6 to 30 carbon atoms, and a heterocyclic group having 2 to 30 carbon atoms.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the number of carbon atoms of a carbonyl group is not particularly limited, but is preferably 1 to 40. Specifically, the carbonyl group may be a compound having the following structures, but is not limited thereto.

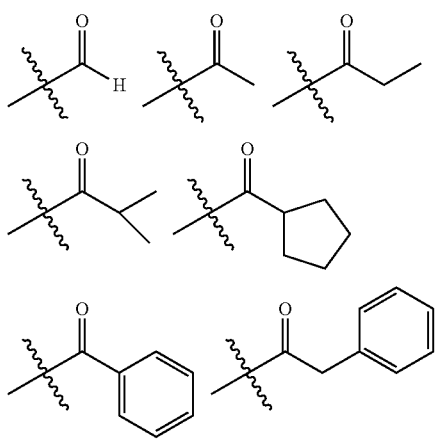

In the present specification, for an ester group, the oxygen of the ester group may be substituted with a straight-chained, branch-chained, or cyclic alkyl group having 1 to 25 carbon atoms, or an aryl group having 6 to 25 carbon atoms. Specifically, the ester group may be a compound having the following structural formulae, but is not limited thereto.

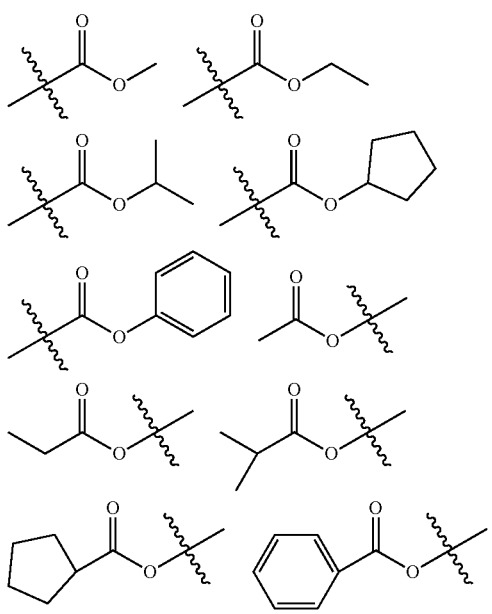

In the present specification, the number of carbon atoms of an imide group is not particularly limited, but is preferably 1 to 25. Specifically, the imide group may be a compound having the following structures, but is not limited thereto.

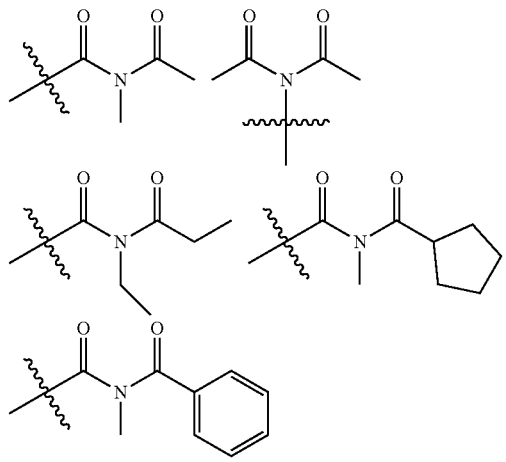

In the present specification, a silyl group may be represented by a formula of —SiRR'R", and R, R', and R" may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a formula of —BRR'R", and R, R', and R" may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, examples of a halogen group include fluorine, chlorine, bromine or iodine.

In the present specification, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a polycyclic heterocyclic group. The heteroarylamine group including two or more heterocyclic groups may include a monocyclic heterocyclic group, a polycyclic heterocyclic group, or both a monocyclic heterocyclic group and a polycyclic heterocyclic group.

In the present specification, an arylheteroarylamine group means an amine group substituted with an aryl group and a heterocyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, a triphenylene group, a fluoranthene group, and the like, but are not limited thereto.

When the fluorenyl group is substituted, the group may be

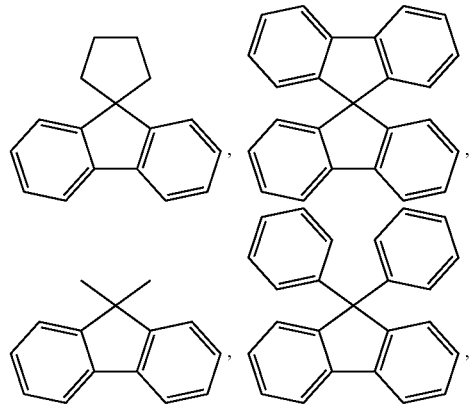

and the like. However, the fluorenyl group is not limited thereto.

In the present specification, a heterocyclic group is a heterocyclic group including one or more of N, O, P, S, Si, and Se as a hetero atom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the above-described description on the heterocyclic group may be applied to a heteroaryl group except for an aromatic group.

In the present specification, the above-described description on the aryl group may be applied to an aryl group in an aryloxy group, an arylthioxy group, an arylsulfoxy group, an arylphosphine group, an aralkyl group, an aralkylamine group, an aralkenyl group, an alkylaryl group, an arylamine group, and an arylheteroarylamine group.

In the present specification, the above-described description on the alkyl group may be applied to an alkyl group in an alkylthioxy group, an alkylsulfoxy group, an aralkyl group, an aralkylamine group, an alkylaryl group, and an alkylamine group.

In the present specification, the above-described description on the heterocyclic group may be applied to a heteroaryl group in a heteroarylamine group, a heteroarylamine group, and an arylheteroarylamine group.

In the present specification, the above-described description on the alkenyl group may be applied to an alkenyl group in an aralkenyl group.

In the present specification, the above-described description on the aryl group may be applied to an arylene except for a divalent arylene group.

In the present specification, the above-described description on the heterocyclic group may be applied to a heteroarylene except for a divalent heteroarylene group.

In the present specification, combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a fused ring thereof.

In the present specification, the aliphatic hydrocarbon ring means a ring composed only of carbon and hydrogen atoms as a ring which is not an aromatic group. In the present specification, examples of an aromatic hydrocarbon ring include a phenyl group, a naphthyl group, an anthracenyl group, and the like, but are not limited thereto.

In the present specification, an aliphatic hetero ring means an aliphatic ring including one or more of hetero atoms.

In the present specification, an aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, Chemical Formula 1 may be represented by the following Chemical Formula 2 or 3.

[Chemical Formula 2]

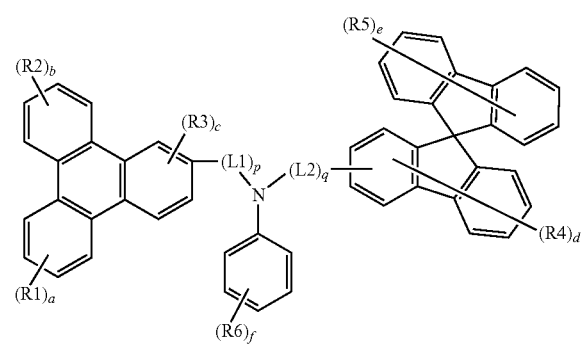

[Chemical Formula 3]

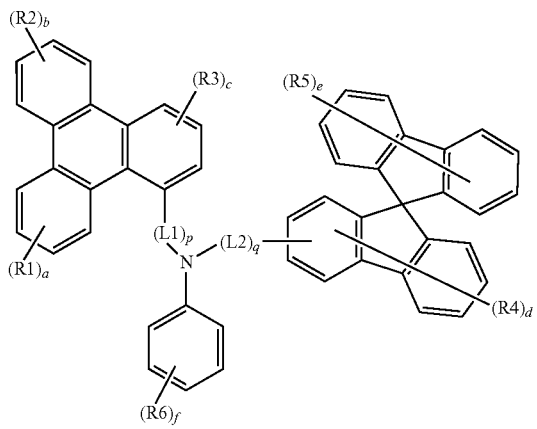

In Chemical Formulae 2 and 3, definitions of L1, L2, R1 to R6, p, q, a, b, c, d, e, and f are the same as those in Chemical Formula 1.

According to an exemplary embodiment of the present specification, Chemical Formula 1 may be represented by any one of the following Chemical Formulae 4 to 6.

[Chemical Formula 4]

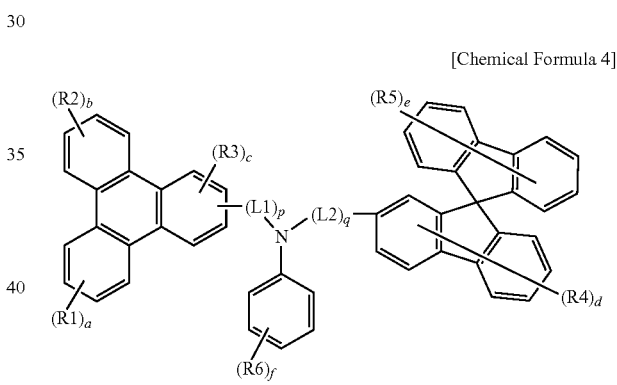

[Chemical Formula 5]

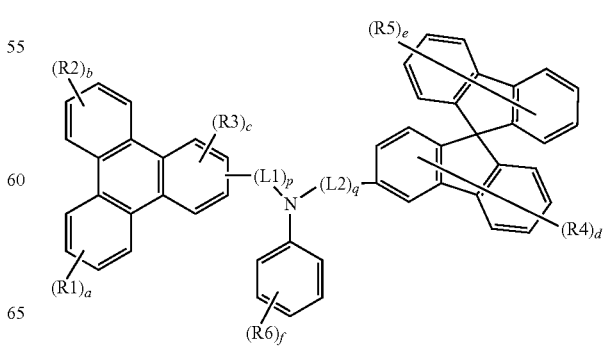

[Chemical Formula 6]

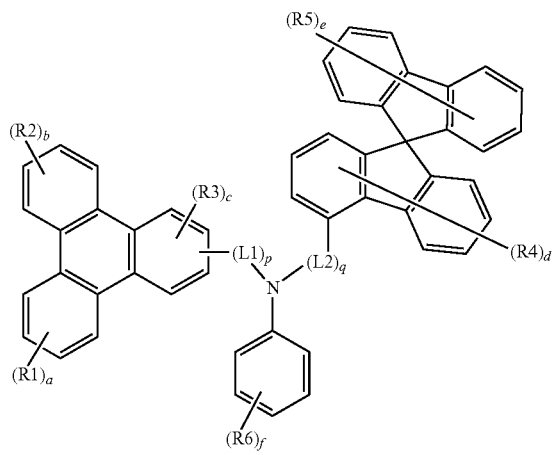

In Chemical Formulae 4 to 6, definitions of L1, L2, R1 to R6, p, q, a, b, c, d, e, and f are the same as those in Chemical Formula 1.

According to an exemplary embodiment of the present specification, Chemical Formula 1 may be represented by any one of the following Chemical Formulae 7 to 9.

[Chemical Formula 7]

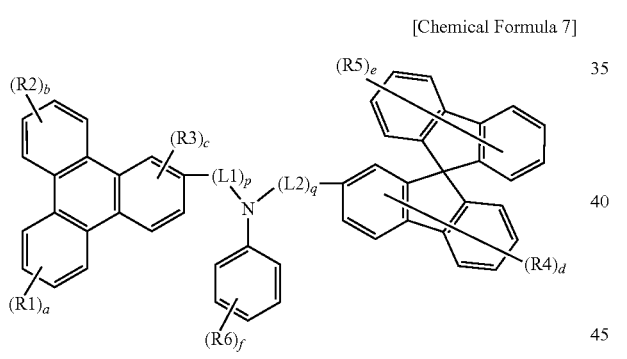

[Chemical Formula 8]

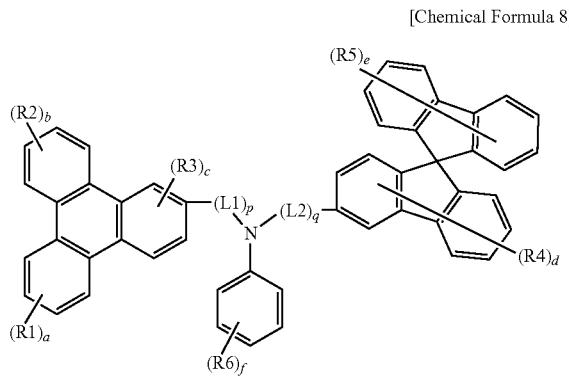

[Chemical Formula 9]

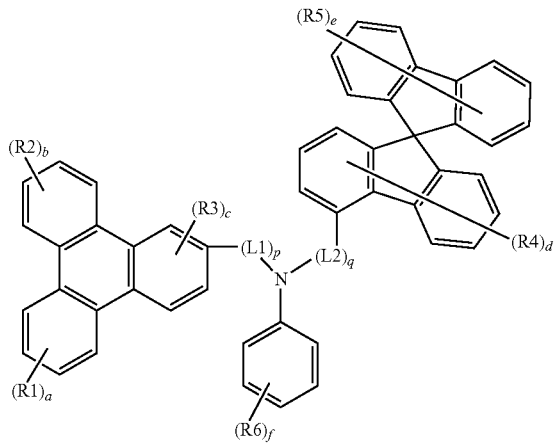

In Chemical Formulae 7 to 9, definitions of L1, L2, R1 to R6, p, q, a, b, c, d, e, and f are the same as those in Chemical Formula 1.

According to an exemplary embodiment of the present specification, Chemical Formula 1 may be represented by any one of the following Chemical Formulae 10 to 12.

[Chemical Formula 10]

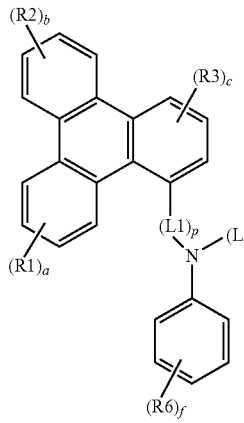

[Chemical Formula 11]

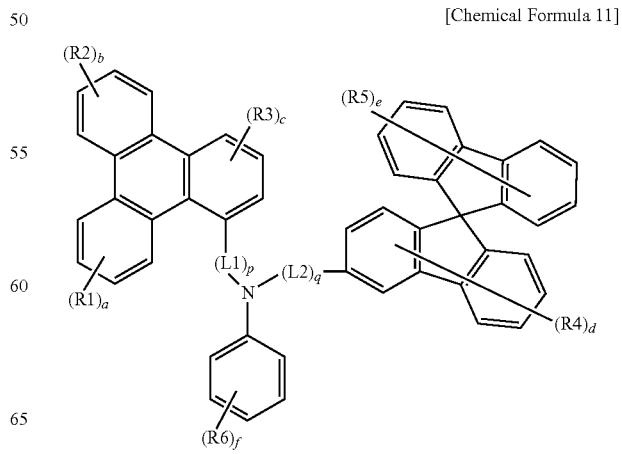

[Chemical Formula 12]

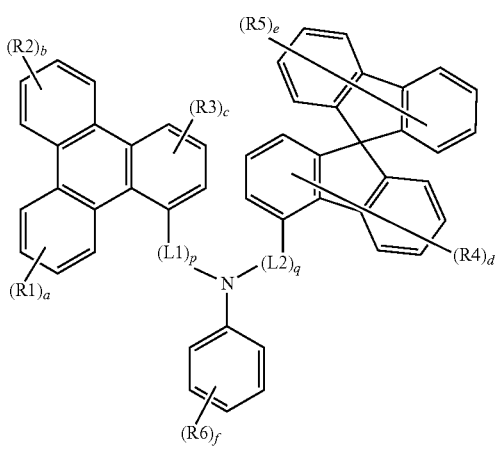

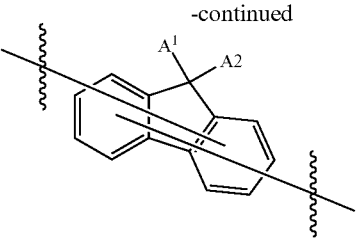

In Chemical Formulae 10 to 12, definitions of L1, L2, R1 to R6, p, q, a, b, c, d, e, and f are the same as those in Chemical Formula 1.

According to an exemplary embodiment of the present specification, L1 and L2 may be a direct bond, or any one selected from the following structures.

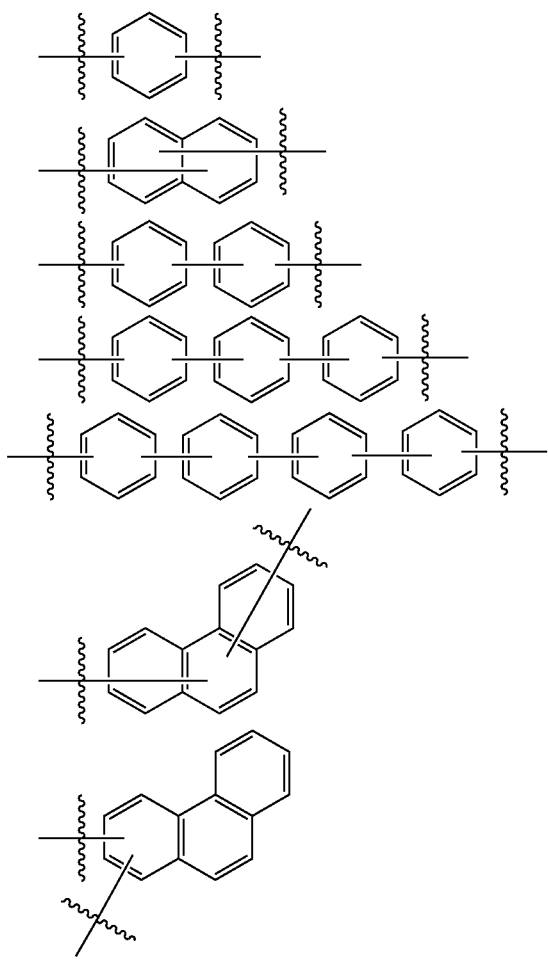

In the structures,

A1 and A2 are the same as or different from each other, and are each independently hydrogen; deuterium; a halogen group; a nitrile group; an alkyl group having 1 to 5 carbon atoms; an aryl group having 6 to 30 carbon atoms; or a heterocyclic group having 2 to 20 carbon atoms, and the structures may be unsubstituted or substituted with one or more substituents selected from the group consisting of deuterium; a halogen group; a nitrile group; a nitro group; a hydroxy group; a carbonyl group; an ester group; an imide group; an amine group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to an exemplary embodiment of the present specification, L1 and L2 are the same as or different from each other, and are each independently a direct bond; or arylene.

According to an exemplary embodiment of the present specification, L1 and L2 are the same as or different from each other, and are each independently a direct bond; or an arylene having 6 to 30 carbon atoms.

According to an exemplary embodiment of the present specification, L1 and L2 are the same as or different from each other, and are each independently a direct bond; or an arylene having 6 to 20 carbon atoms.

According to an exemplary embodiment of the present specification, L1 and L2 are the same as or different from each other, and are each independently a direct bond; or an arylene having 6 to 18 carbon atoms.

According to an exemplary embodiment of the present specification, L1 and L2 are the same as or different from each other, and are each independently a direct bond; or a monocyclic to tetracyclic arylene.

According to an exemplary embodiment of the present specification, L1 and L2 are the same as or different from each other, and are each independently a direct bond; phenylene; naphthylene; biphenylylene; terphenylene; phenanthrylene; or fluorenylene.

According to an exemplary embodiment of the present specification, L1 and L2 are the same as or different from each other, and are each independently a direct bond; or a substituted or unsubstituted phenylene.

According to an exemplary embodiment of the present specification, L1 and L2 are the same as or different from each other, and are each independently a direct bond; or a phenylene which is unsubstituted or substituted with one or more substituents selected from the group consisting of deuterium, a halogen group, a nitrile group, an alkyl group having 1 to 5 carbon atoms, an aryl group having 6 to 30 carbon atoms, and a heterocyclic group having 2 to 30 carbon atoms.

According to an exemplary embodiment of the present specification, L1 and L2 are the same as or different from each other, and are each independently a direct bond; or phenylene.

According to an exemplary embodiment of the present specification, L1 and L2 are a direct bond.

According to an exemplary embodiment of the present specification, L1 is a direct bond, and L2 is phenylene.

According to an exemplary embodiment of the present specification, L1 is phenylene, and L2 is a direct bond.

According to an exemplary embodiment of the present specification, the

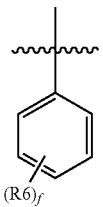

moiety may be represented by any one selected from the following structures.

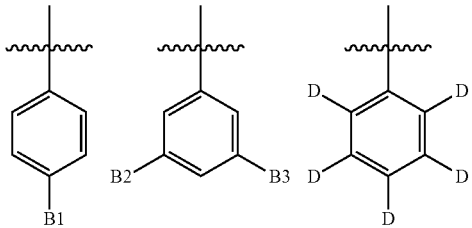

In the structures,

B1 to B3 are the same as or different from each other, and are each independently hydrogen; deuterium; a halogen group; a nitrile group; an alkyl group; or a silyl group substituted with an alkyl group.

According to an exemplary embodiment of the present specification, B1 to B3 are the same as or different from each other, and are each independently hydrogen; deuterium; a halogen group; a nitrile group; an alkyl group having 1 to 10 carbon atoms; or a silyl group substituted with an alkyl group having 1 to 10 carbon atoms.

According to an exemplary embodiment of the present specification, B1 to B3 are the same as or different from each other, and are each independently hydrogen; deuterium; a halogen group; a nitrile group; an alkyl group having 1 to 5 carbon atoms; or a silyl group substituted with an alkyl group having 1 to 5 carbon atoms.

According to an exemplary embodiment of the present specification, B1 to B3 are the same as or different from each other, and are each independently hydrogen; deuterium; a halogen group; a nitrile group; an alkyl group having 1 to 5 carbon atoms; or a trimethylsilyl group.

According to an exemplary embodiment of the present specification, R6 is hydrogen; deuterium; a halogen group; a nitrile group; an alkyl group; or a silyl group substituted with an alkyl group.

According to an exemplary embodiment of the present specification, R6 is hydrogen; deuterium; a halogen group; a nitrile group; an alkyl group having 1 to 5 carbon atoms; or a silyl group substituted with an alkyl group having 1 to 5 carbon atoms.

According to an exemplary embodiment of the present specification, R6 is hydrogen; deuterium; a halogen group; a nitrile group; an alkyl group having 1 to 5 carbon atoms; or a trimethylsilyl group.

According to an exemplary embodiment of the present specification, R1 to R5 are hydrogen.

According to an exemplary embodiment of the present specification, R1 to R6 are hydrogen.

According to an exemplary embodiment of the present specification, p and q are the same as or different from each other, and are each independently 0 or 1.

According to an exemplary embodiment of the present specification, the compound of Chemical Formula 1 may be any one selected from the following compounds.

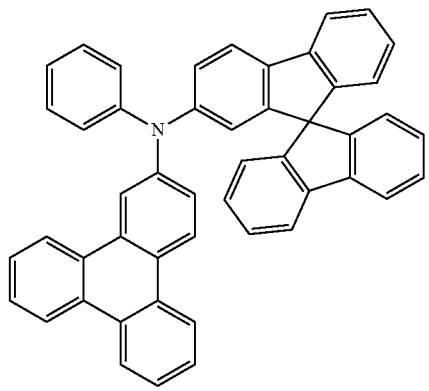

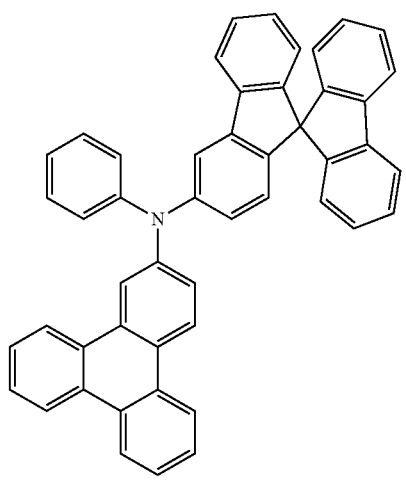

3
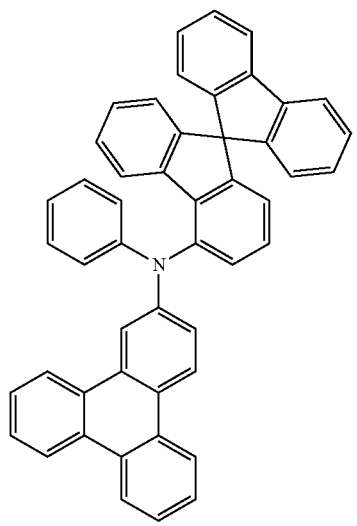
4
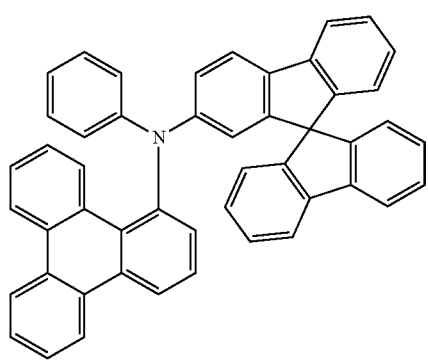
5
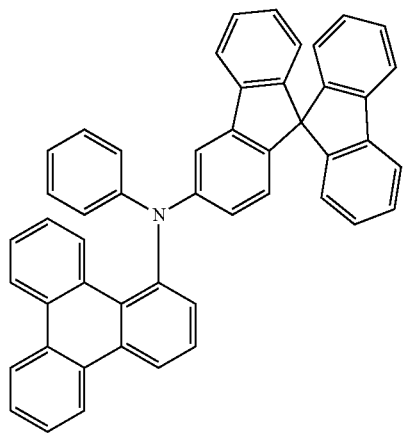
6
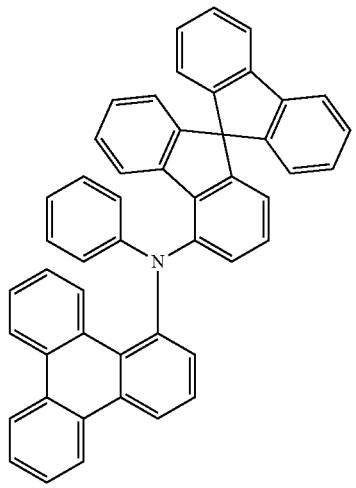
7
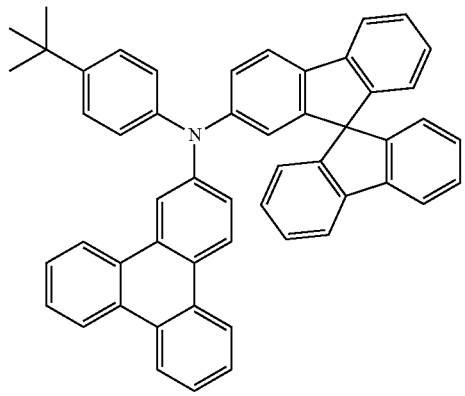
8
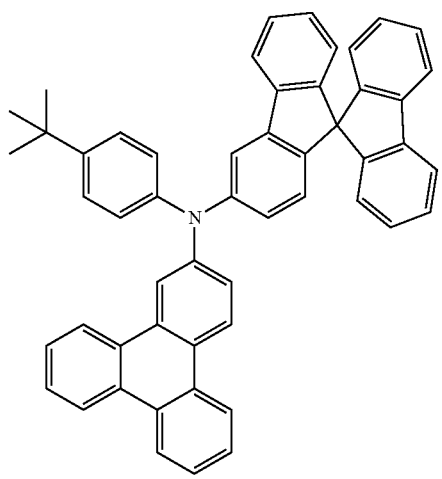

-continued
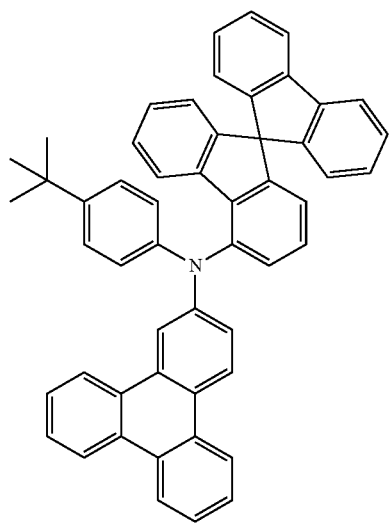
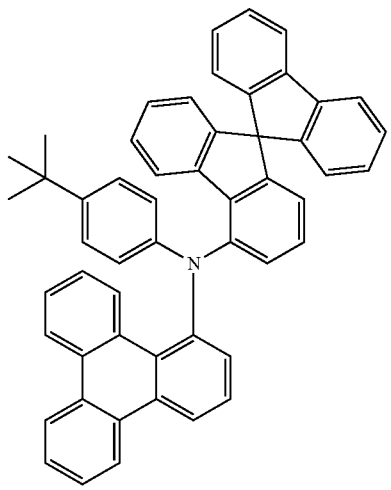
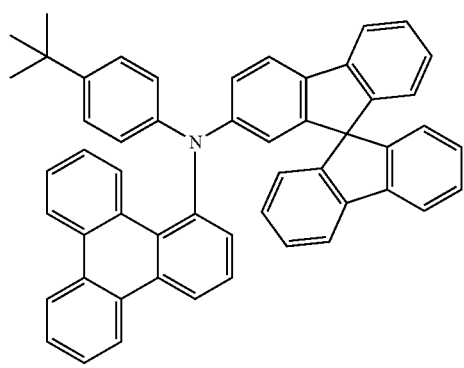
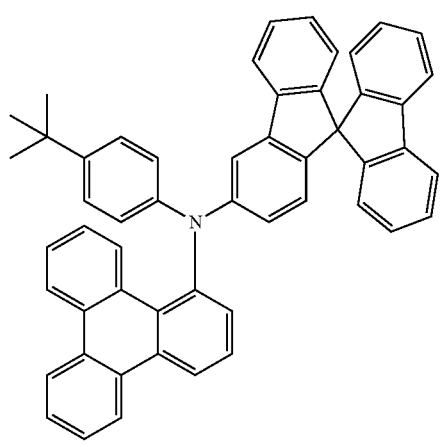
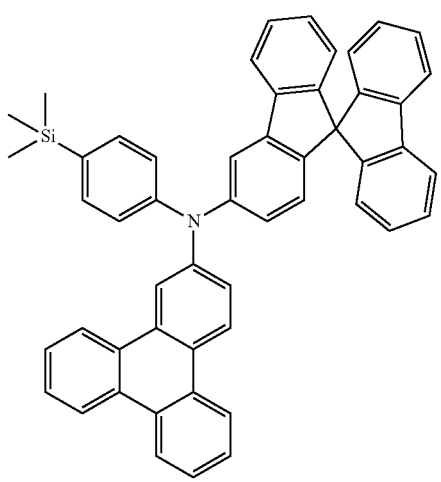

15
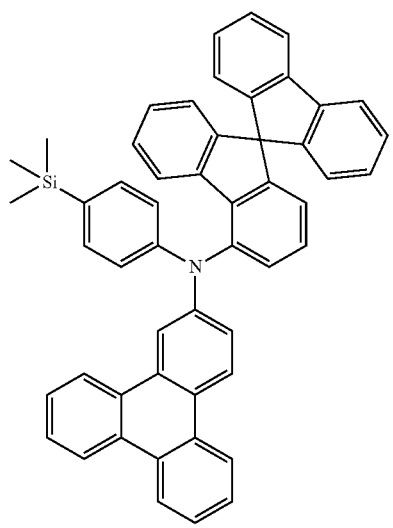
16
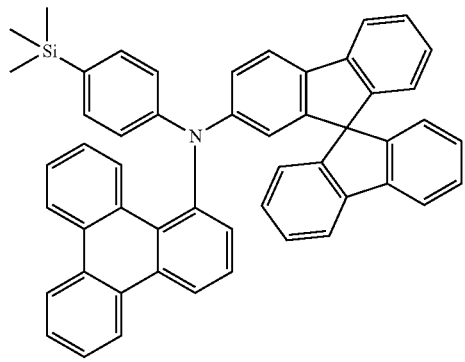
17
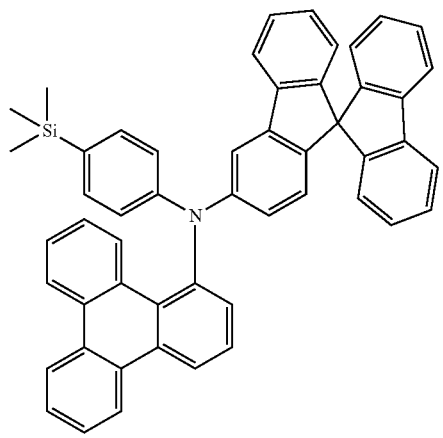
18
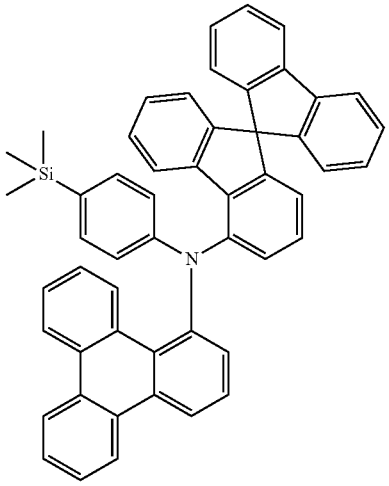
19
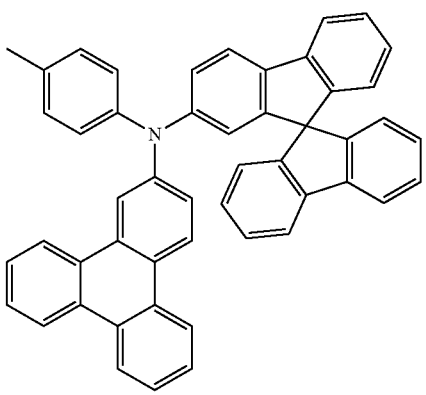
20
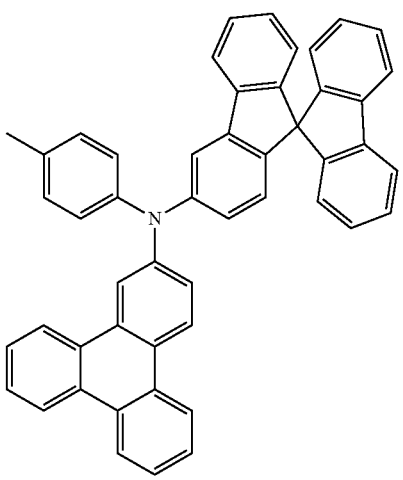

21
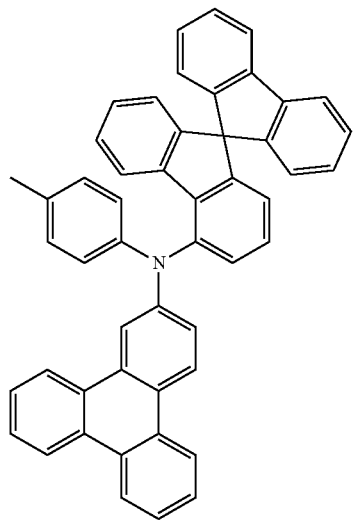
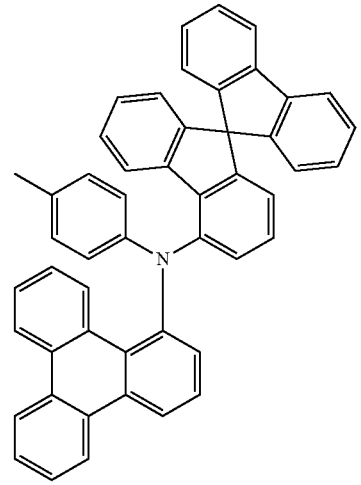
22
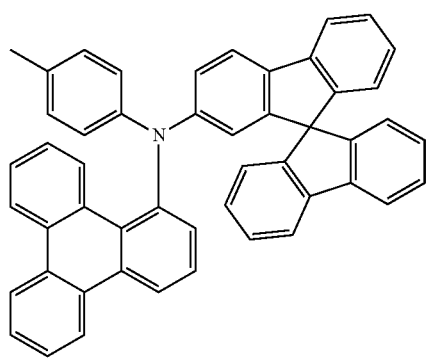
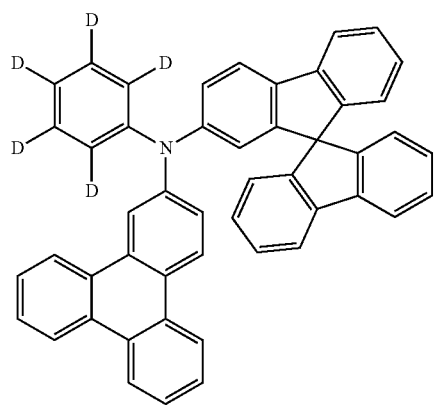
23
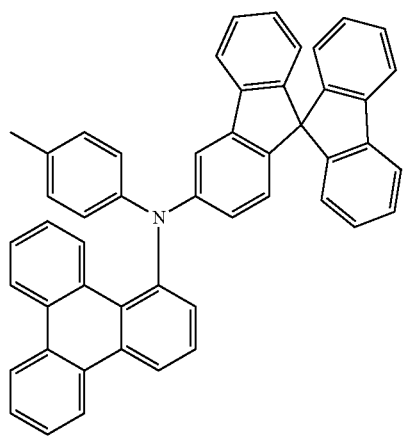
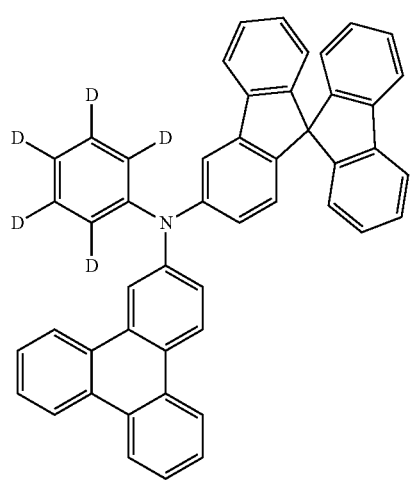

27
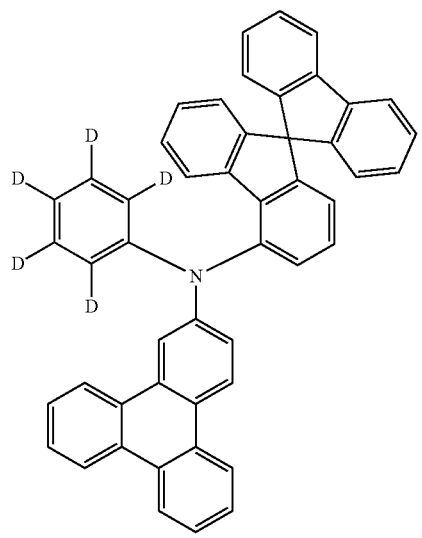
28
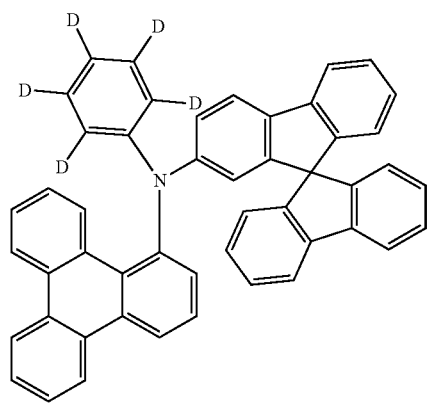
29
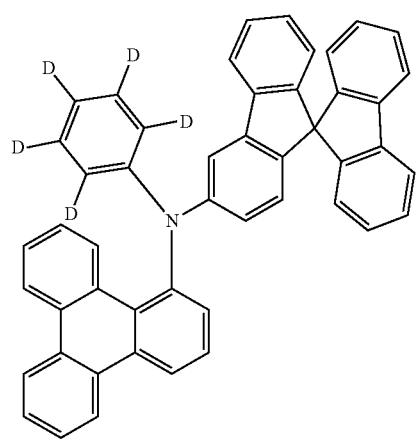
30
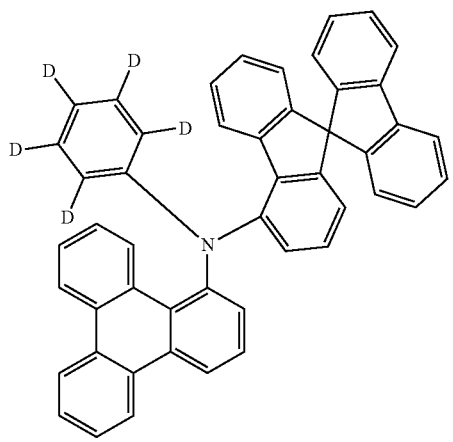
31
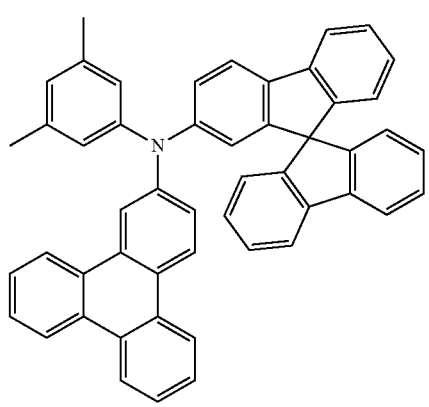
32
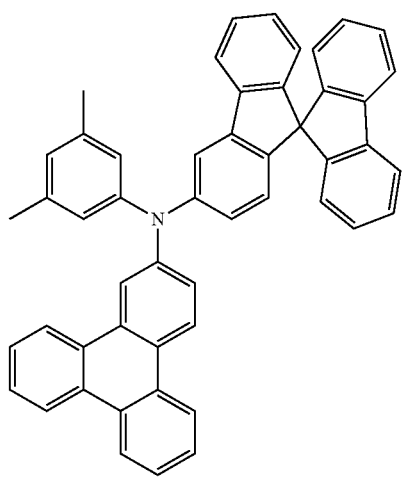

33
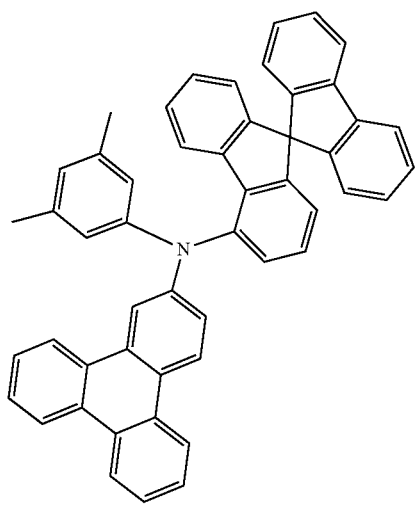
34
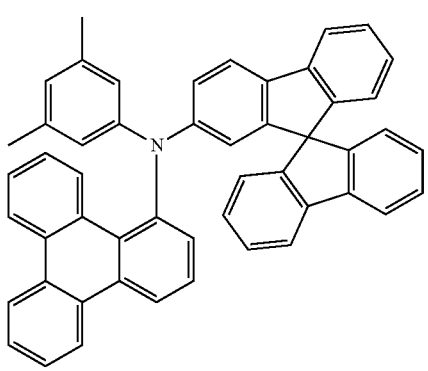
35
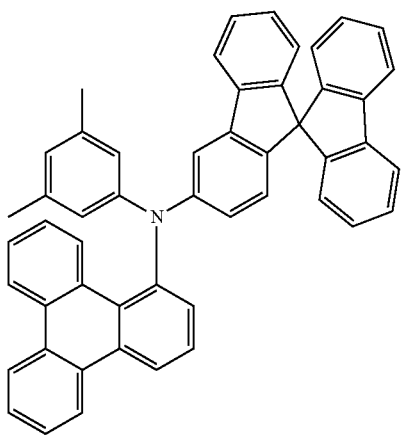
36
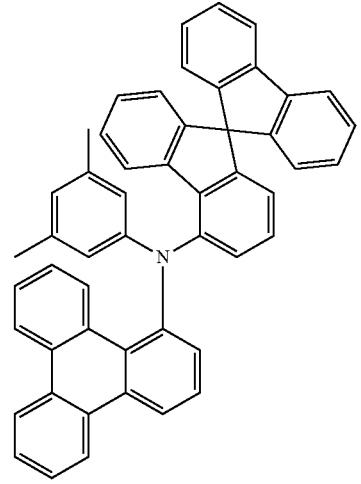
37
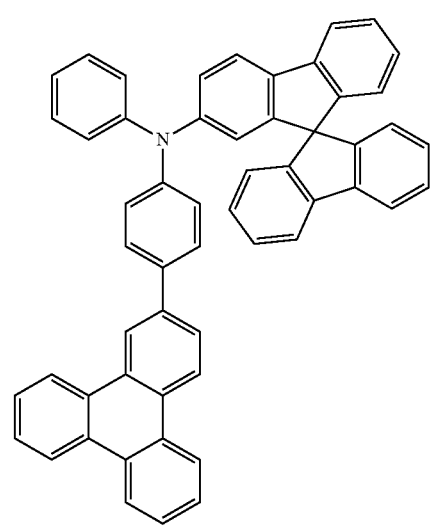
38
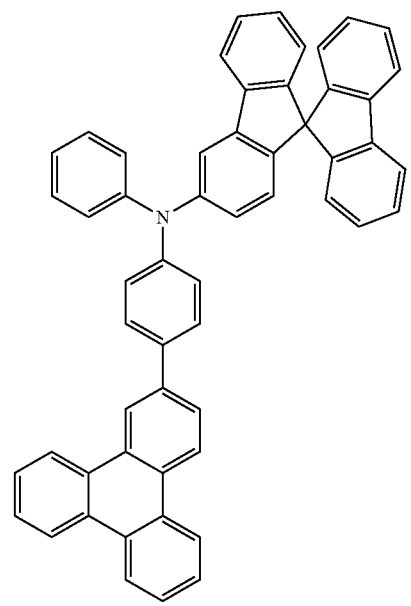

39
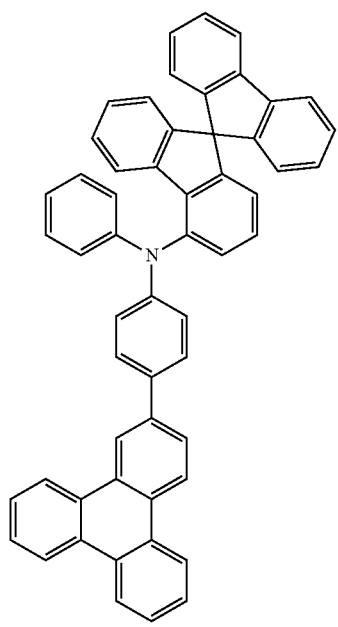
40
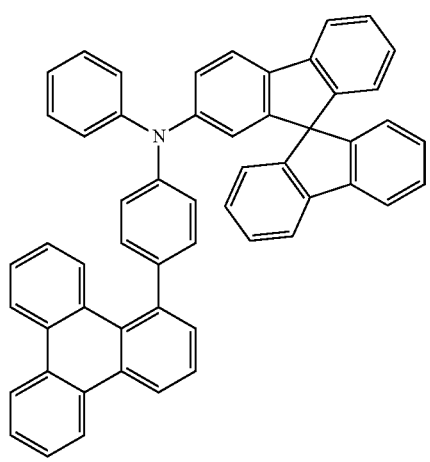
41
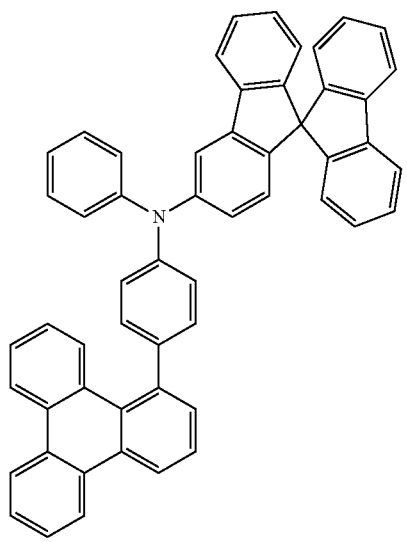
42
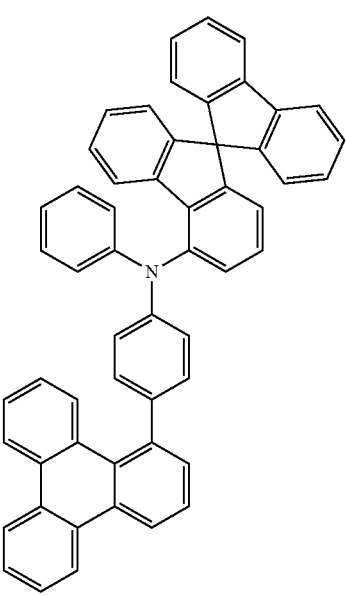
43
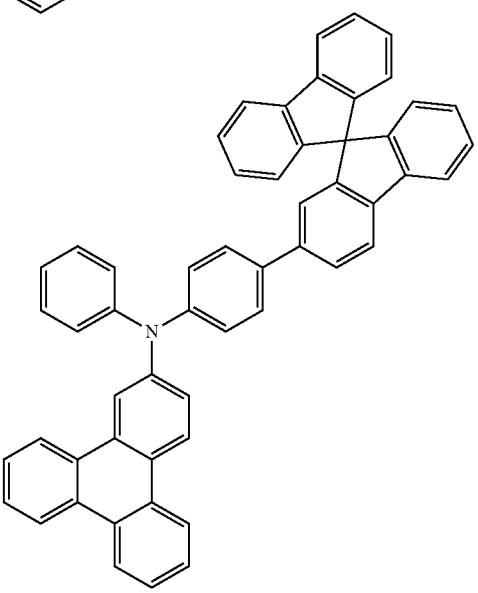
44
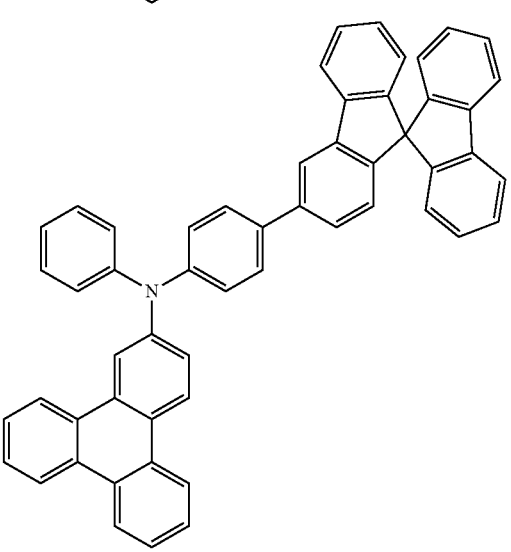

45
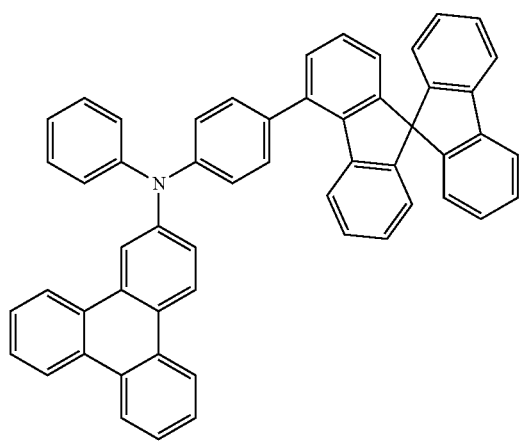
46
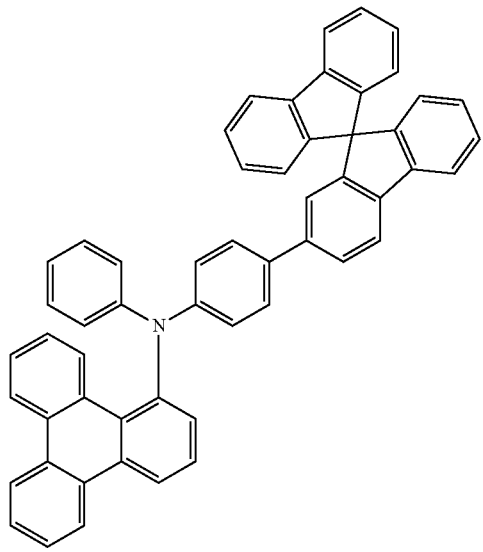
47
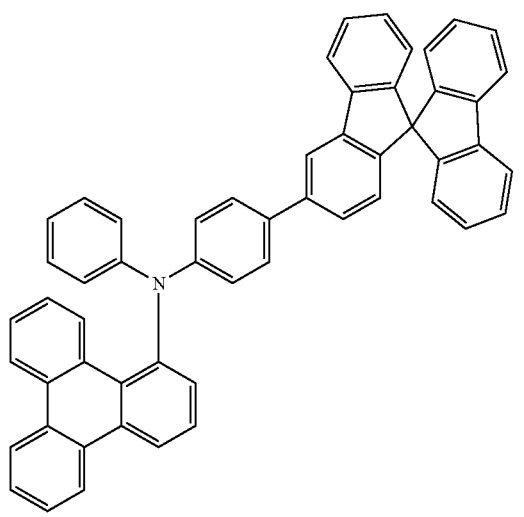
48
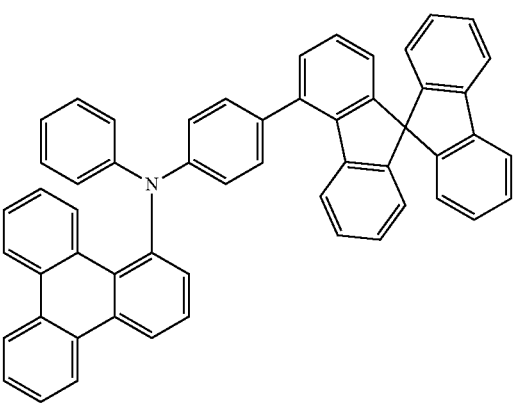
49
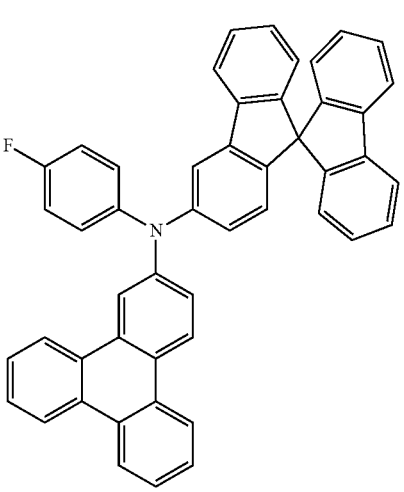
50

51
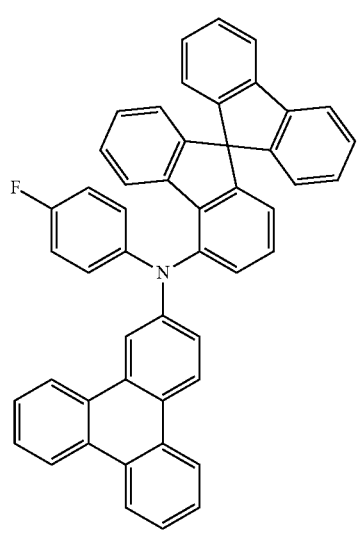
52
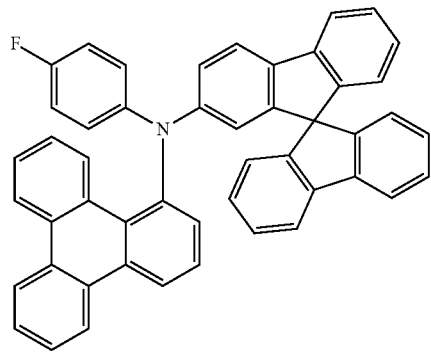
53
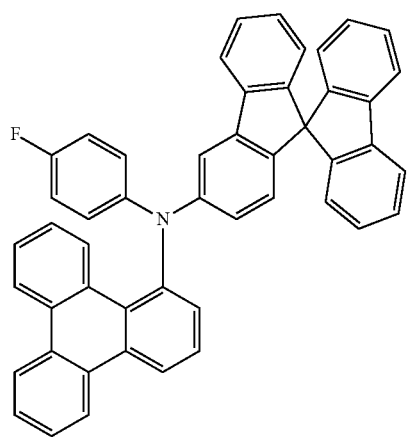
54
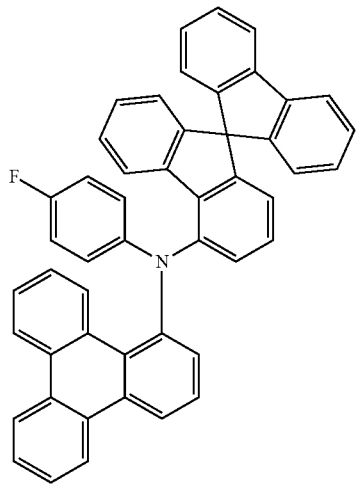
55
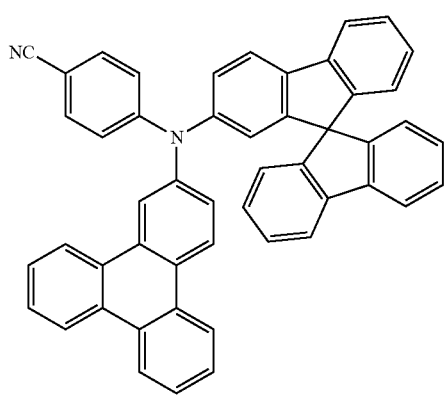
56
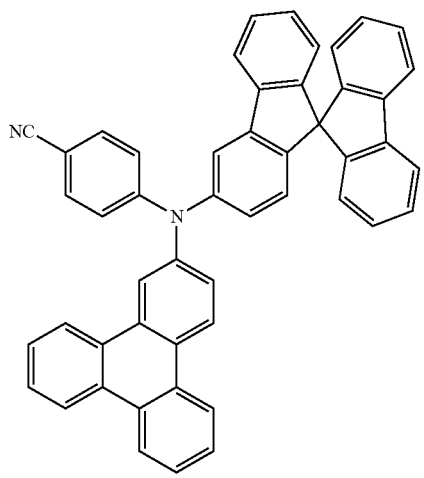

57
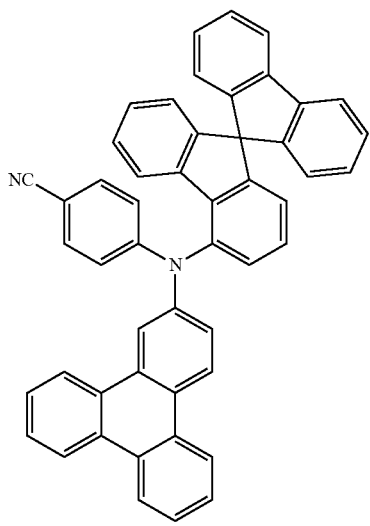
58
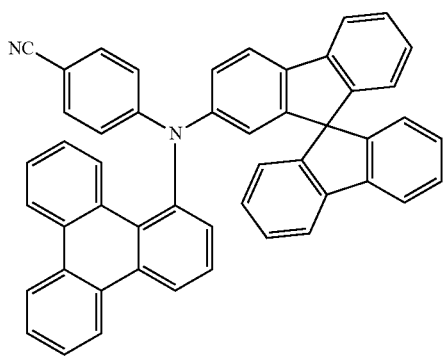
59
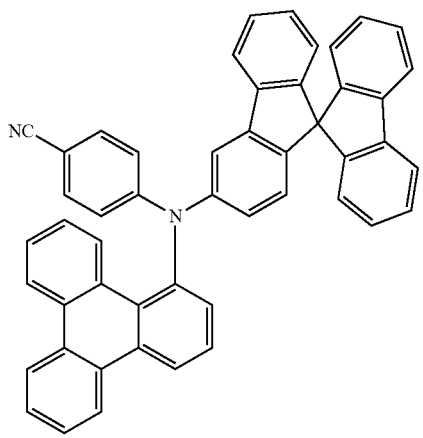
60
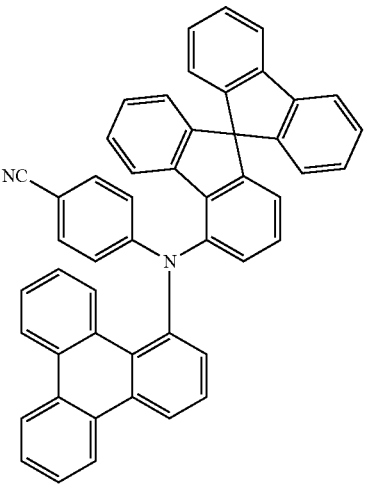
The compound represented by Chemical Formula 1 may be prepared based on the Preparation Examples to be described below.
According to an exemplary embodiment of the present specification, the compound may be prepared by the method such as the following Reaction Formulae 1-1 and 1-2.
[Reaction Formula 1-1]
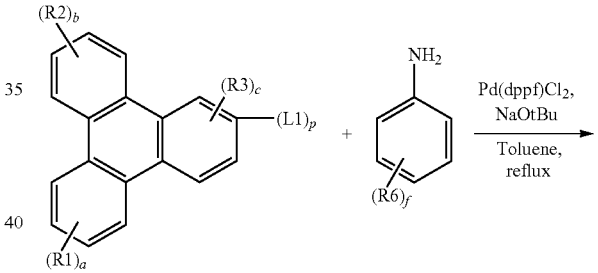
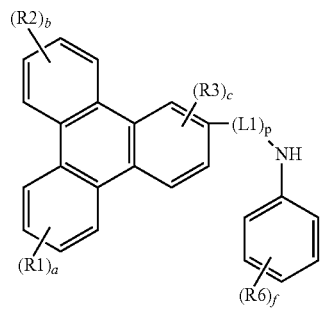
[Reaction Formula 1-2]
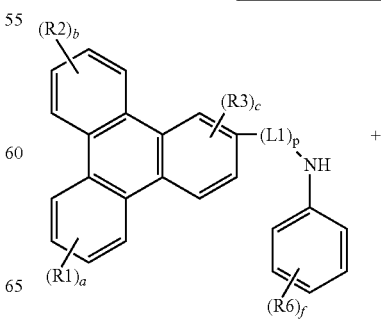

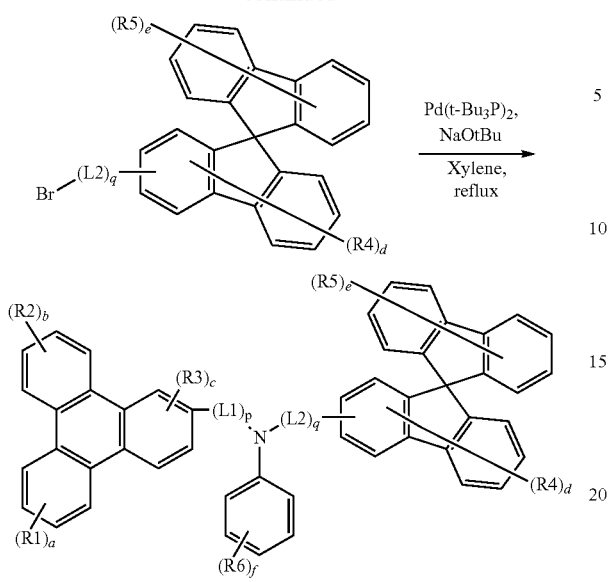

In Reaction Formulae 1-1 and 1-2, the definitions of the substituents are the same as those described above. Further, according to an exemplary embodiment of the present specification, the compound may be prepared by the method such as the following Reaction Formulae 2-1 and 2-2.

[Reaction Formula 2-1]

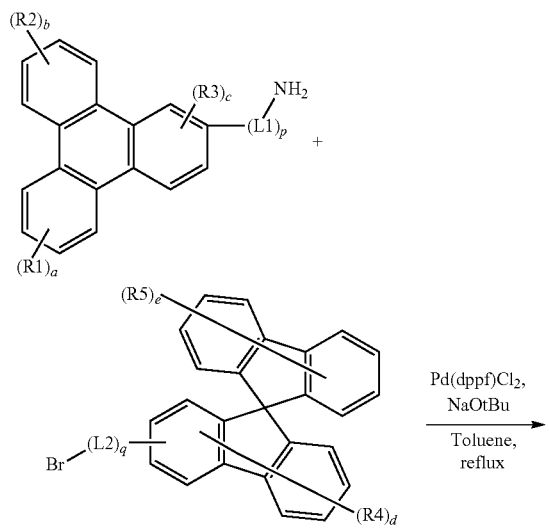

[Reaction Formula 2-2]

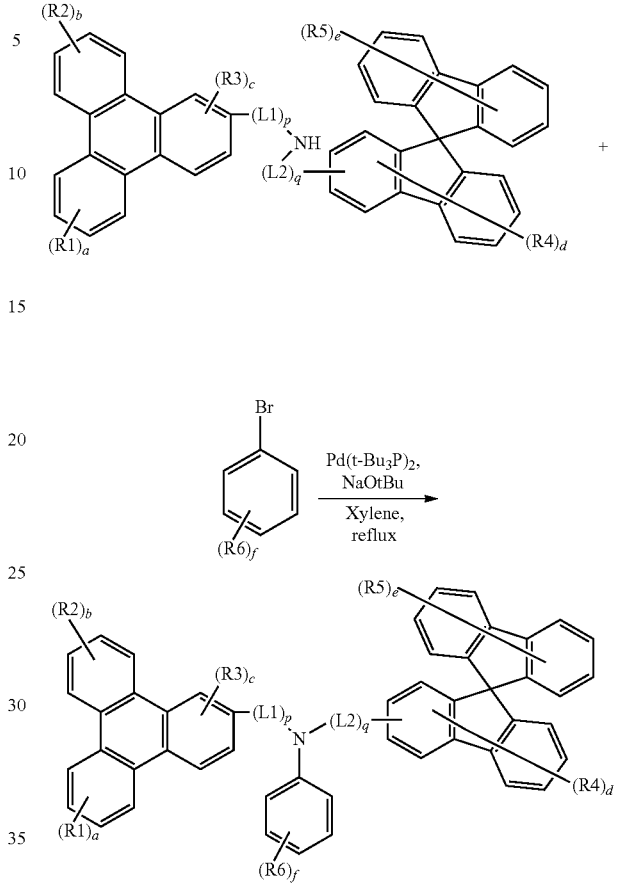

In Reaction Formulae 2-1 and 2-2, the definitions of the substituents are the same as those described above.

In addition, according to an exemplary embodiment of the present specification, the compound may be prepared by the process such as the following Reaction Formulae 3-1 to 3-3.

[Reaction Formula 3-1]

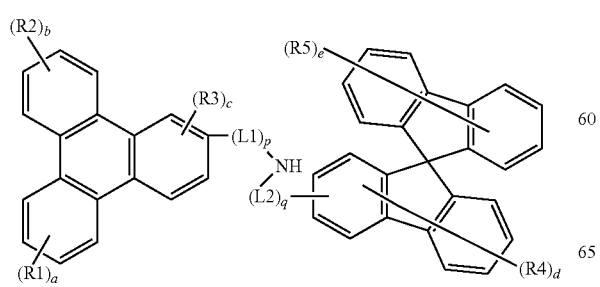

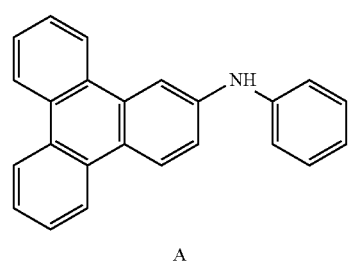

A

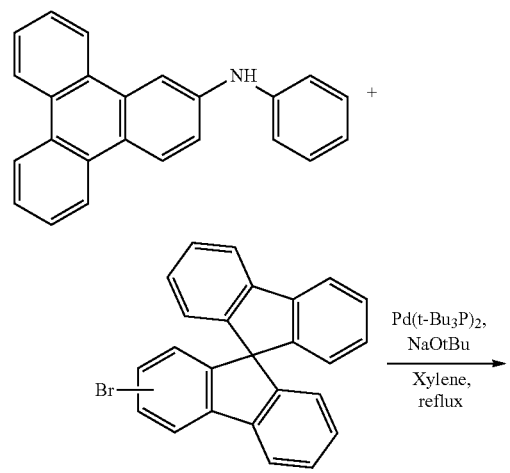
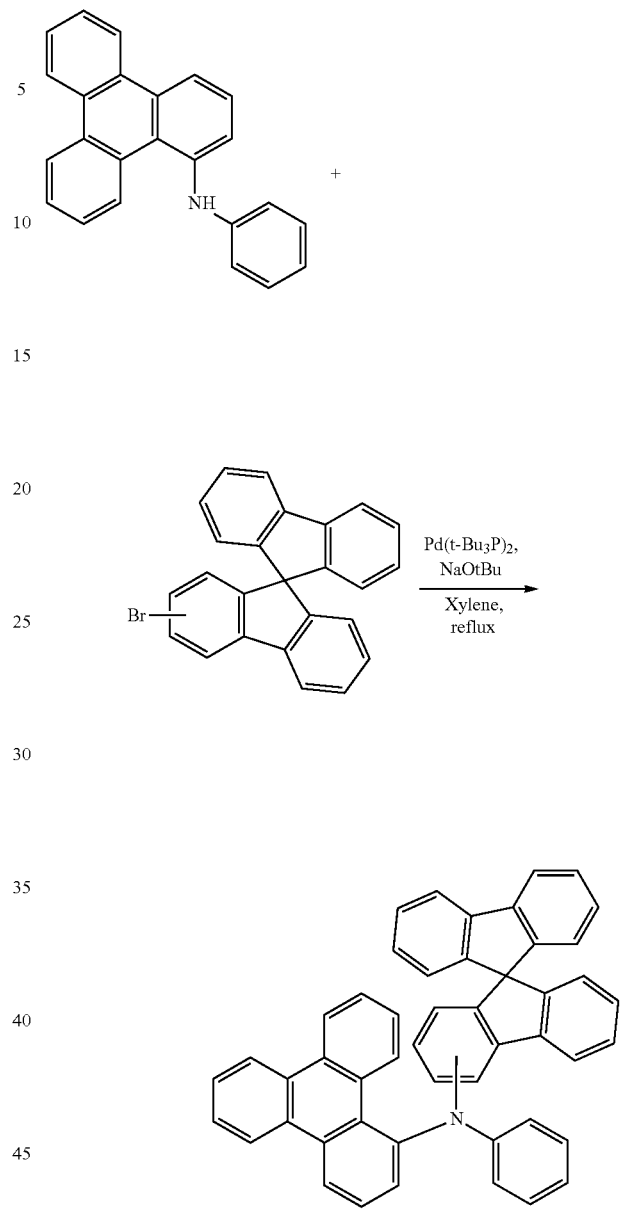
[Reaction Formula 3-2]
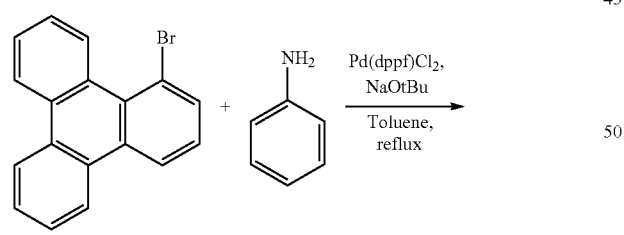
[Reaction Formula 3-3]
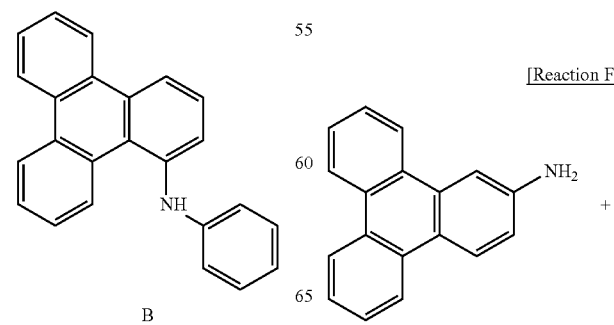

-continued

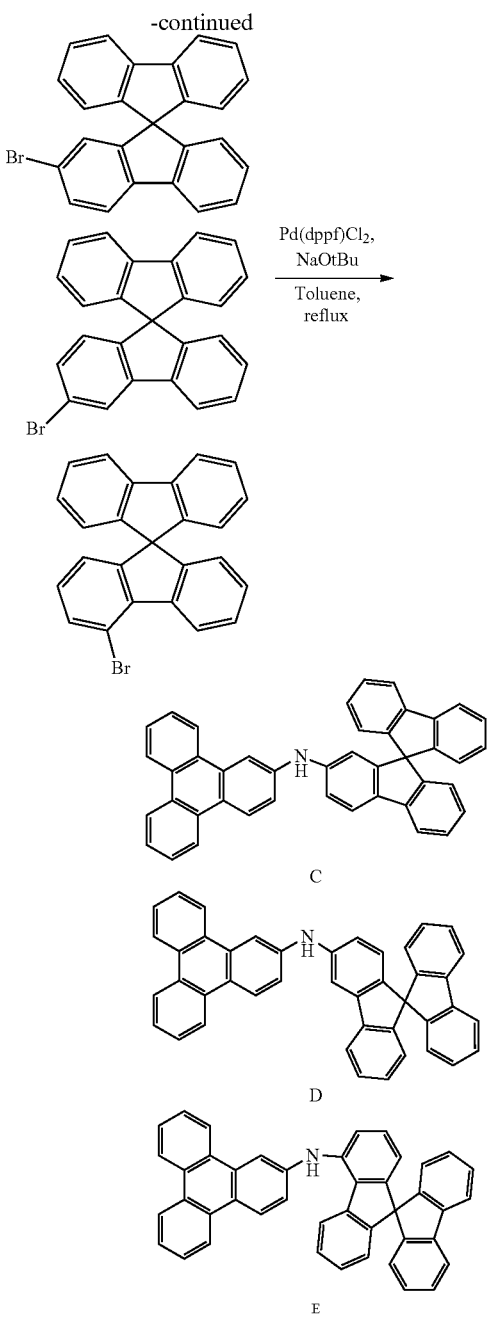

Furthermore, the present specification provides an organic light emitting device including the compound represented by Chemical Formula 1.

An exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transport layer, an electron blocking layer, a light emitting layer, an electron transport layer, an electron injection layer, and the like as organic material layers. However, the structure of the organic light emitting device is not limited thereto, and may include a fewer number of organic layers.

In an exemplary embodiment of the present specification, the organic material layer includes a hole injection layer, a hole transport layer, or a layer which simultaneously injects and transports holes, and the hole injection layer, the hole transport layer, or the layer which simultaneously injects and transports holes includes the compound of Chemical Formula 1.

Further, in an exemplary embodiment of the present specification, the organic material layer includes a hole injection layer, a hole transport layer, an electron blocking layer, or a layer which simultaneously injects and transports holes, and the hole injection layer, the hole transport layer, the electron blocking layer, or the layer which simultaneously injects and transports holes includes the compound of Chemical Formula 1.

In another exemplary embodiment, the organic material layer includes a light emitting layer, and the light emitting layer includes the compound of Chemical Formula 1.

In an exemplary embodiment of the present specification, the organic material layer includes an electron transport layer or an electron injection layer, and the electron transport layer or the electron injection layer includes the compound of Chemical Formula 1.

In an exemplary embodiment of the present specification, the electron transport layer, the electron injection layer, or the layer which simultaneously transports and injects electrons includes the compound of Chemical Formula 1.

In another exemplary embodiment, the organic material layer includes a light emitting layer and an electron transport layer, and the electron transport layer includes the compound of Chemical Formula 1.

In still another exemplary embodiment, the organic light emitting device may be an organic light emitting device having a structure (normal type) in which a positive electrode, one or more organic material layers, and a negative electrode are sequentially stacked on a substrate.

In yet another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present specification is exemplified in FIGS. 1 and 2.

FIG. 1 illustrates an example of an organic light emitting device composed of a substrate 1, a positive electrode 2, a light emitting layer 3, and a negative electrode 4. In the structure as described above, the compound may be included in the light emitting layer.

FIG. 2 illustrates an example of an organic light emitting device composed of a substrate 1, a positive electrode 2, a hole injection layer 5, a hole transport layer 6, a light emitting layer 7, an electron transport layer 8, and a negative electrode 4. In the structure as described above, the compound may be included in one or more of the hole injection layer, the hole transport layer, the light emitting layer, and the electron transport layer.

The organic light emitting device of the present specification may be manufactured by the materials and methods known in the art, except that one or more layers of the organic material layers include the compound of the present specification, that is, the compound of Chemical Formula 1.

When the organic light emitting device includes a plurality of organic material layers, the organic material layers may be formed of the same material or different materials.

An exemplary embodiment of the present specification provides an organic light emitting device including: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the heterocyclic compound. In one exemplary embodiment, as the two or more organic material layers, two or more may be selected from the group consisting of an electron transport layer, an electron injection layer, a layer which simultaneously transports and injects electrons, and a hole blocking layer.

In an exemplary embodiment of the present specification, the organic material layer includes two or more electron transport layers, and at least one of the two or more electron transport layers includes the heterocyclic compound. Specifically, in an exemplary embodiment of the present specification, the heterocyclic compound may also be included in one layer of the two or more electron transport layers, and may be included in each of the two or more electron transport layers.

In addition, in an exemplary embodiment of the present specification, when the heterocyclic compound is included in each of the two or more electron transporting layers, the other materials except for the heterocyclic compound may be the same as or different from each other.

According to an exemplary embodiment of the present specification, the organic material layer includes a light emitting layer, and the light emitting layer includes a compound represented by the following Chemical Formula 1-A.

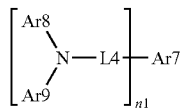

[Chemical Formula 1-A]

In Chemical Formula 1-A, n1 is an integer of 1 or more,

Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L4 is a direct bond; a substituted or unsubstituted arylene group; or a substituted or unsubstituted heteroarylene group, Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L4 is a direct bond.

According to an exemplary embodiment of the present specification, n1 is 2.

In an exemplary embodiment of the present specification, Ar7 is a divalent pyrene group which is unsubstituted or substituted with deuterium, a methyl group, an ethyl group, or a tert-butyl group.

According to an exemplary embodiment of the present specification, Ar8 and Ar9 are the same as or different from each other, and are each independently a substituted or unsubstituted aryl group having 6 to 30 carbon atoms.

According to an exemplary embodiment of the present specification, Ar8 and Ar9 are the same as or different from each other, and are each independently an aryl group which is unsubstituted or substituted with a germanium group substituted with an alkyl group.

According to an exemplary embodiment of the present specification, Ar8 and Ar9 are the same as or different from each other, and are each independently an aryl group which is unsubstituted or substituted with a trimethylgermanium group.

According to an exemplary embodiment of the present specification, Ar8 and Ar9 are the same as or different from each other, and are each independently a substituted or unsubstituted phenyl group.

According to an exemplary embodiment of the present specification, Ar8 and Ar9 are a phenyl group which is unsubstituted or substituted with a trimethylgermanium group.

According to an exemplary embodiment of the present specification, Chemical Formula 1-A is represented by the following compound.

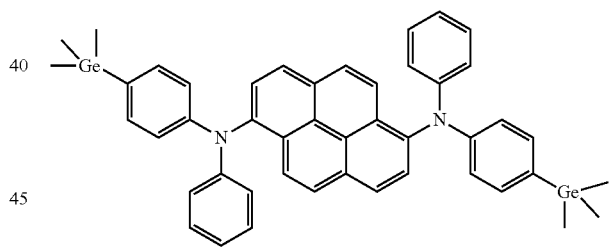

According to an exemplary embodiment of the present specification, the organic material layer includes a light emitting layer, and the light emitting layer includes a compound represented by the following Chemical Formula 2-A.

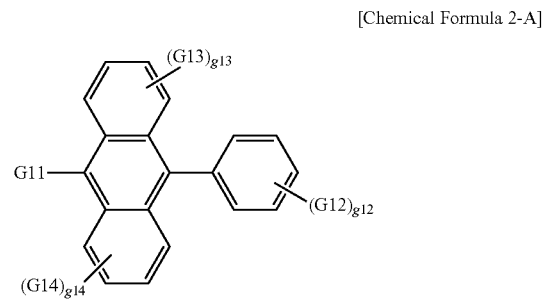

[Chemical Formula 2-A]

In Chemical Formula 2-A,

G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

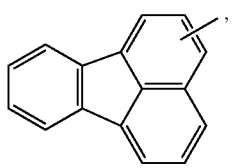

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, G11 is a 1-naphthyl group.

According to an exemplary embodiment of the present specification, G12 is a 2-naphthyl group.

According to an exemplary embodiment of the present specification, G13 and G14 are hydrogen.

According to an exemplary embodiment of the present specification, Chemical Formula 2-A is represented by the following compound.

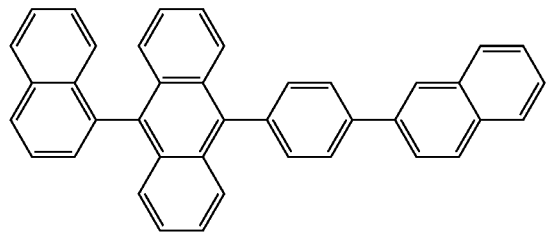 [SMILES: c1ccc2cc(-c3ccc(-c4c5ccccc5c(-c5cccc6ccccc56)c5ccccc45)cc3)ccc2c1]

The organic light emitting device of the present specification may be manufactured by the materials and methods known in the art, except that one or more layers of the organic material layers include the compound of Chemical Formula 1, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto. In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO$_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or LiO$_2$/Al, and the like, but are not limited thereto. The hole injection layer is a layer which injects holes from an electrode, and a hole injection material is preferably a compound which has a capability of transporting holes, and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes transported from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include: an 8-hydroxy-quinoline aluminum complex (Alq$_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material is suitably a material which may receive electrons well from a negative electrode and transfer the electrons to a light emitting layer, and has a large mobility for electrons. Specific examples thereof include: an Al complex of 8-hydroxyquinoline; a complex including Alq$_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Chemical Formula 1 may be included in an organic solar cell or an organic transistor in addition to an organic light emitting device.

The preparation of the compound represented by Chemical Formula 1 and the organic light emitting device including the same will be specifically described in the following Examples. However, the following Examples are provided for exemplifying the present specification, and the scope of the present specification is not limited thereby.

<Preparation Example 1> Synthesis of the Following Compound 1-1

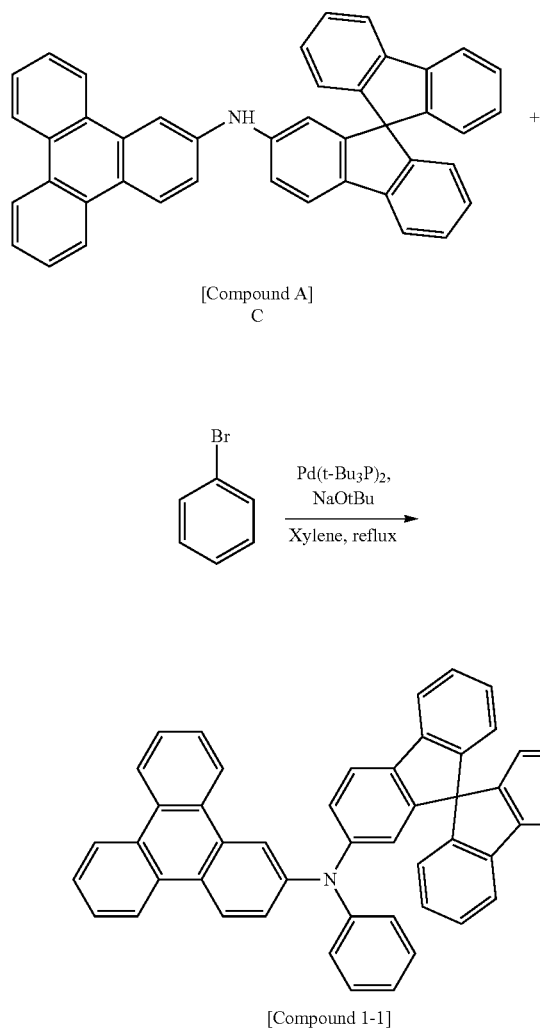

[Compound 1-1]

<Preparation Example 2> Synthesis of the Following Compound 1-2

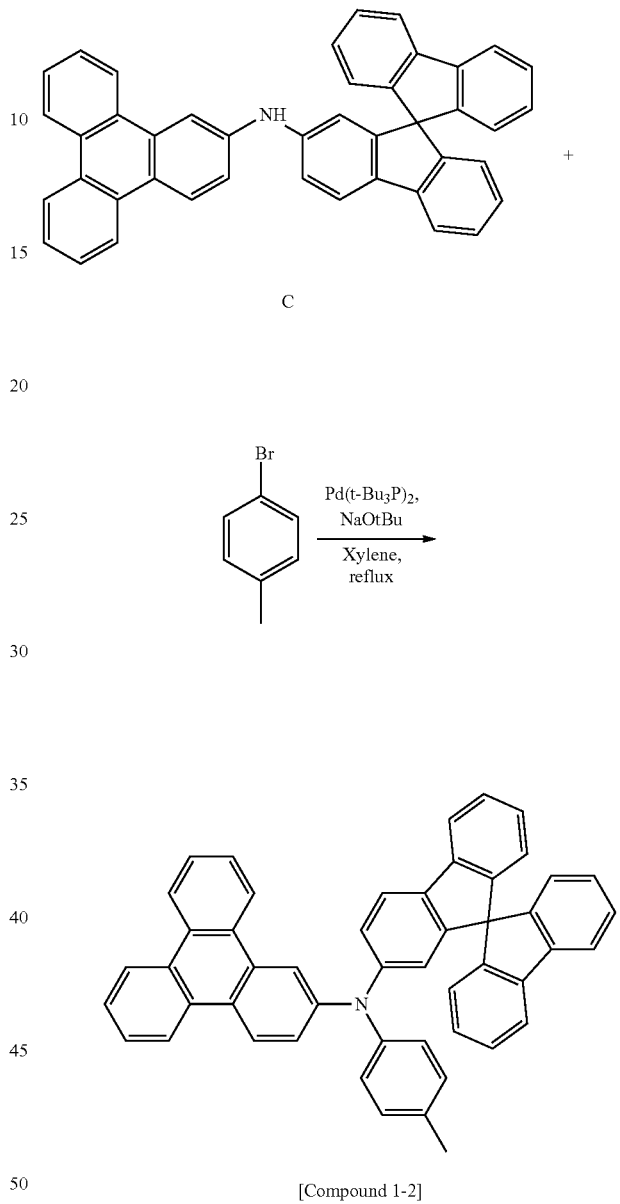

[Compound 1-2]

Under a nitrogen atmosphere, Compound C (10.0 g, 17.57 mmol) and bromobenzene (3.02 g, 19.33 mmol) were completely dissolved in 180 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 260 ml of ethyl acetate to prepare Compound 1-1 (8.36 g, yield: 75%).

MS[M+H]$^+$=634

Under a nitrogen atmosphere, Compound C (10.0 g, 17.57 mmol) and 1-bromo-4-methylbenzene (3.23 g, 19.33 mmol) were completely dissolved in 160 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 260 ml of ethyl acetate to prepare Compound 1-2 (8.14 g, yield: 73%).

MS[M+H]$^+$=648

<Preparation Example 3> Synthesis of the Following Compound 1-3

<Preparation Example 4> Synthesis of the Following Compound 1-4

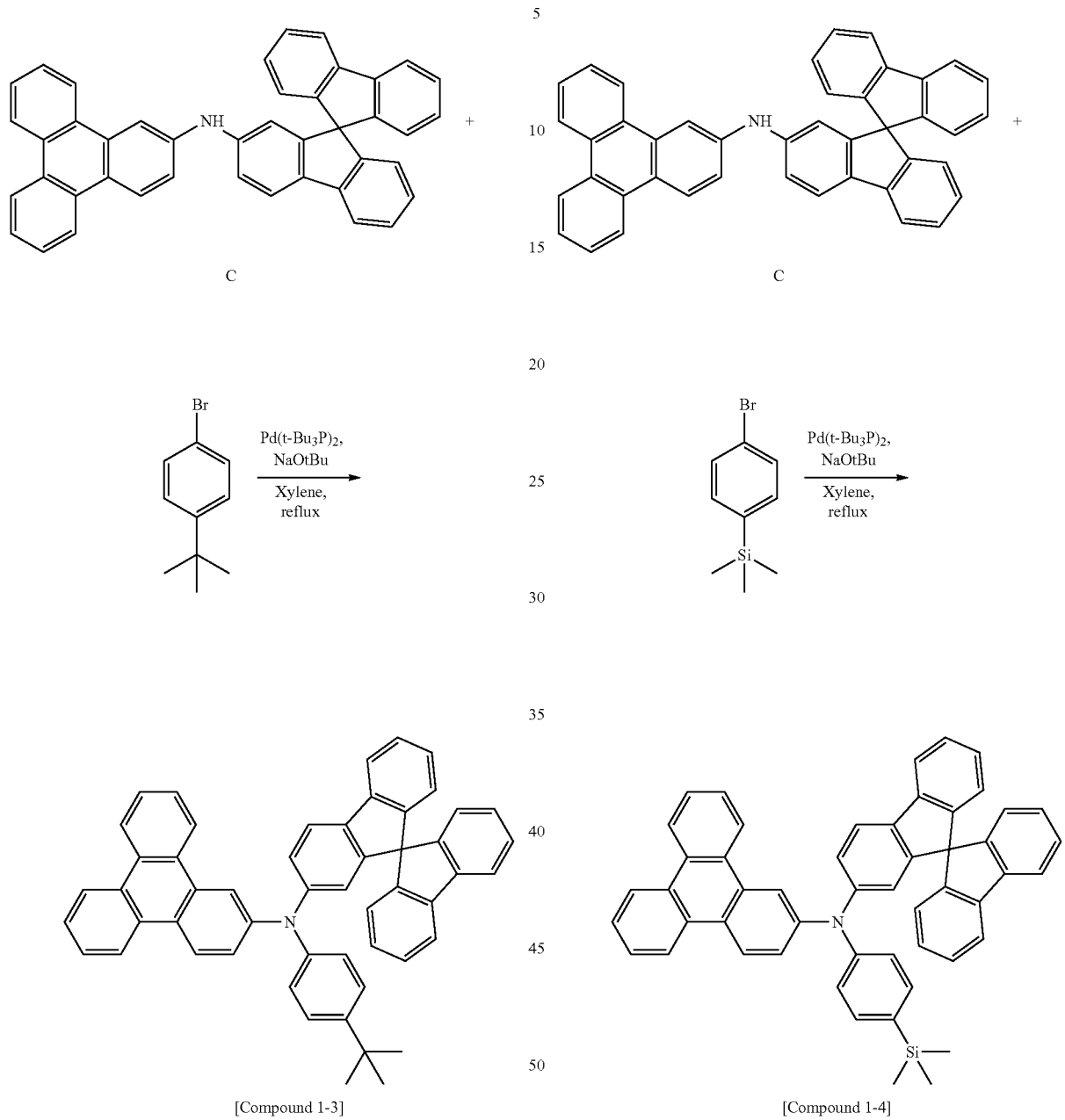

[Compound 1-3]

[Compound 1-4]

Under a nitrogen atmosphere, Compound C (10.0 g, 17.57 mmol) and 1-bromo-4-tert-butylbenzene (4.03 g, 19.33 mmol) were completely dissolved in 170 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 260 ml of ethyl acetate to prepare Compound 1-3 (7.14 g, yield: 64%).

MS[M+H]$^+$=690

Under a nitrogen atmosphere, Compound C (10.0 g, 17.57 mmol) and (4-bromophenyl)trimethylsilane (4.33 g, 19.33 mmol) were completely dissolved in 170 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 260 ml of ethyl acetate to prepare Compound 1-4 (7.64 g, yield: 67%).

MS[M+H]$^+$=706

\<Preparation Example 5\> Synthesis of the Following Compound 1-5

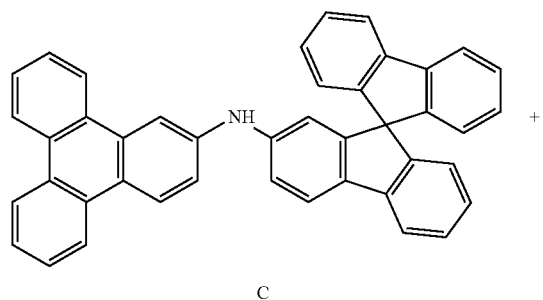

C

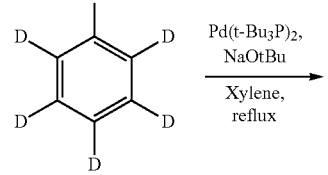

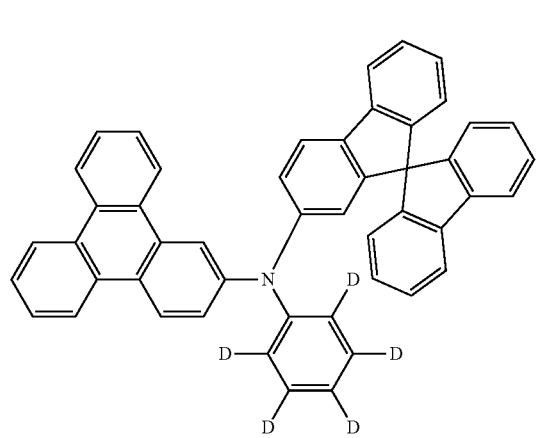

[Compound 1-5]

Under a nitrogen atmosphere, Compound C (10.0 g, 17.57 mmol) and 1-bromobenzene-2,3,4,5,6-d5 (3.06 g, 19.33 mmol) were completely dissolved in 190 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 5 hours. The temperature was lowered to normal temperature, the mixture was filtered to remove the base, and then xylene was concentrated under reduced pressure, and the residue was recrystallized with 230 ml of ethyl acetate to prepare Compound 1-5 (9.56 g, yield: 85%).

MS[M+H]$^+$=639

\<Preparation Example 6\> Synthesis of the Following Compound 1-6

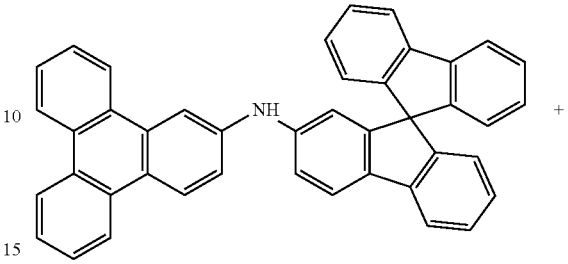

C

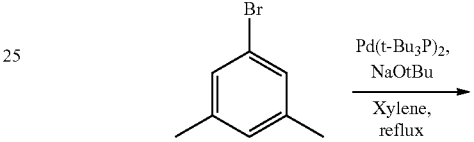

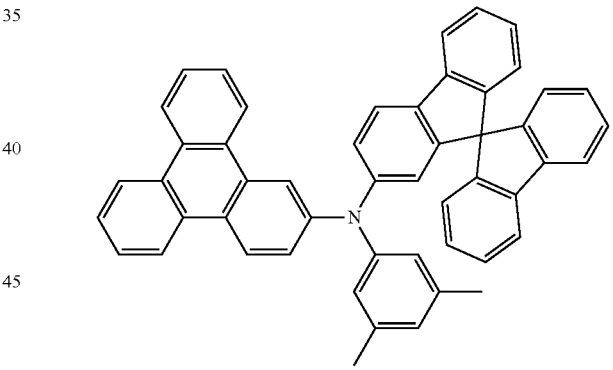

[Compound 1-6]

Under a nitrogen atmosphere, Compound C (10.0 g, 17.57 mmol) and 1-bromo-3,5-dimethylbenzene (3.49 g, 19.33 mmol) were completely dissolved in 190 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 2 hours. The temperature was lowered to normal temperature, the mixture was filtered to remove the base, and then xylene was concentrated under reduced pressure, and the residue was recrystallized with 260 ml of ethyl acetate to prepare Compound 1-6 (8.65 g, yield: 74%).

MS[M+H]$^+$=662

<Preparation Example 7> Synthesis of the Following Compound 1-7

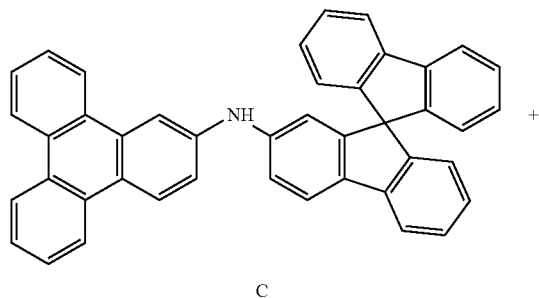

C

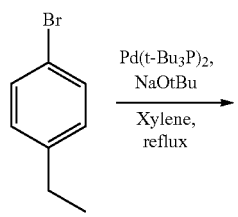

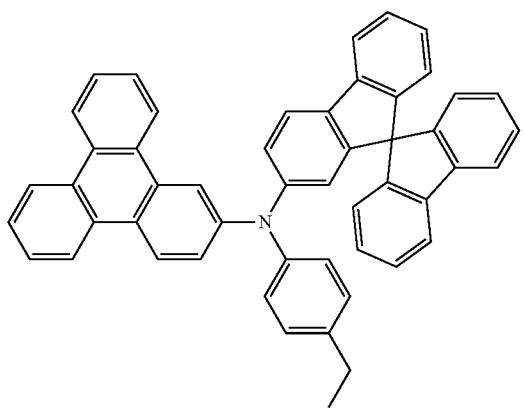

[Compound 1-7]

Under a nitrogen atmosphere, Compound C (10.0 g, 17.57 mmol) and 1-bromo-4-ethylbenzene (3.49 g, 19.33 mmol) were completely dissolved in 150 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 5 hours. The temperature was lowered to normal temperature, the mixture was filtered to remove the base, and then xylene was concentrated under reduced pressure, and the residue was recrystallized with 230 ml of ethyl acetate to prepare Compound 1-7 (8.14 g, yield: 73%).

MS[M+H]$^+$=662

<Preparation Example 8> Synthesis of the Following Compound 1-8

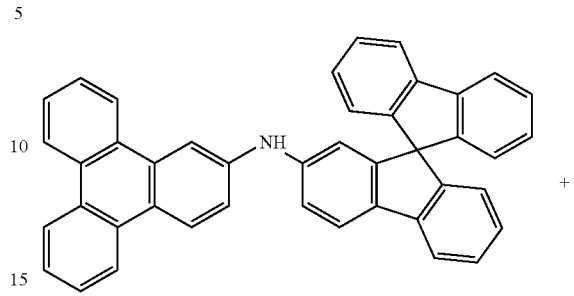

C

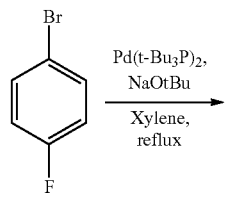

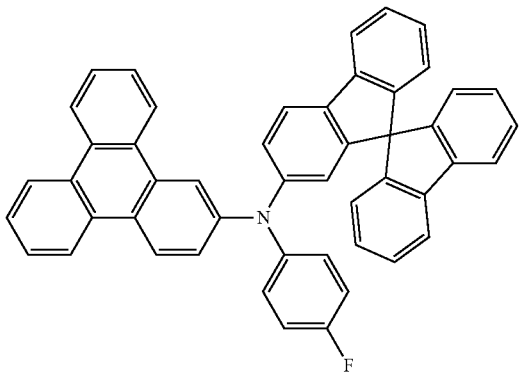

[Compound 1-8]

Under a nitrogen atmosphere, Compound C (10.0 g, 17.57 mmol) and 1-bromo-4-fluorobenzene (3.31 g, 19.33 mmol) were completely dissolved in 150 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 5 hours. The temperature was lowered to normal temperature, the mixture was filtered to remove the base, and then xylene was concentrated under reduced pressure, and the residue was recrystallized with 230 ml of ethyl acetate to prepare Compound 1-8 (8.14 g, yield: 73%).

MS[M+H]$^+$=652

<Preparation Example 9> Synthesis of the Following Compound 1-9

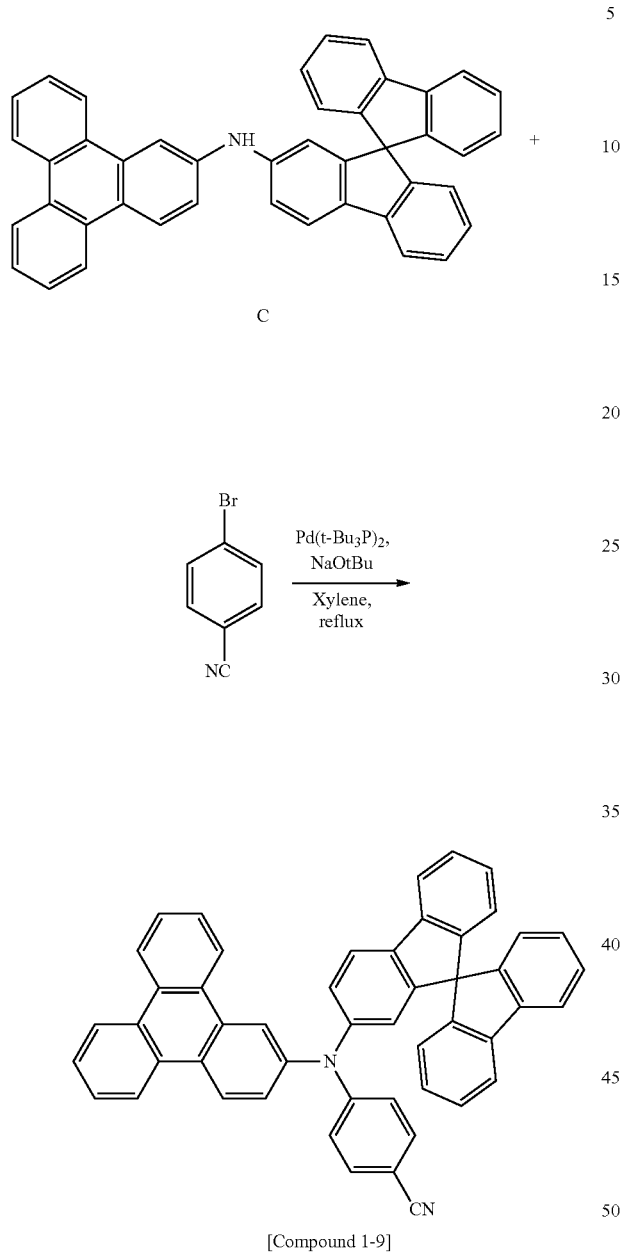

[Compound 1-9]

Under a nitrogen atmosphere, Compound C (10.0 g, 17.57 mmol) and 4-bromobenzonitrile (3.44 g, 19.33 mmol) were completely dissolved in 160 ml of xylene in a 500 ml-round bottom flask, and then sodium tert-butoxide (2.19 g, 22.84 mol) was added thereto, bis(tri-tert-butylphosphine) palladium(0) (0.09 g, 0.18 mmol) was put thereinto, and then the resulting mixture was heated and stirred for 6 hours. The temperature was lowered to normal temperature, the mixture was filtered to remove the base, and then xylene was concentrated under reduced pressure, and the residue was recrystallized with 210 ml of ethyl acetate to prepare Compound 1-9 (8.14 g, yield: 73%).

MS[M+H]$^+$=659

<Preparation Example 10>—Synthesis of the Following Compounds 1-10 to 1-18

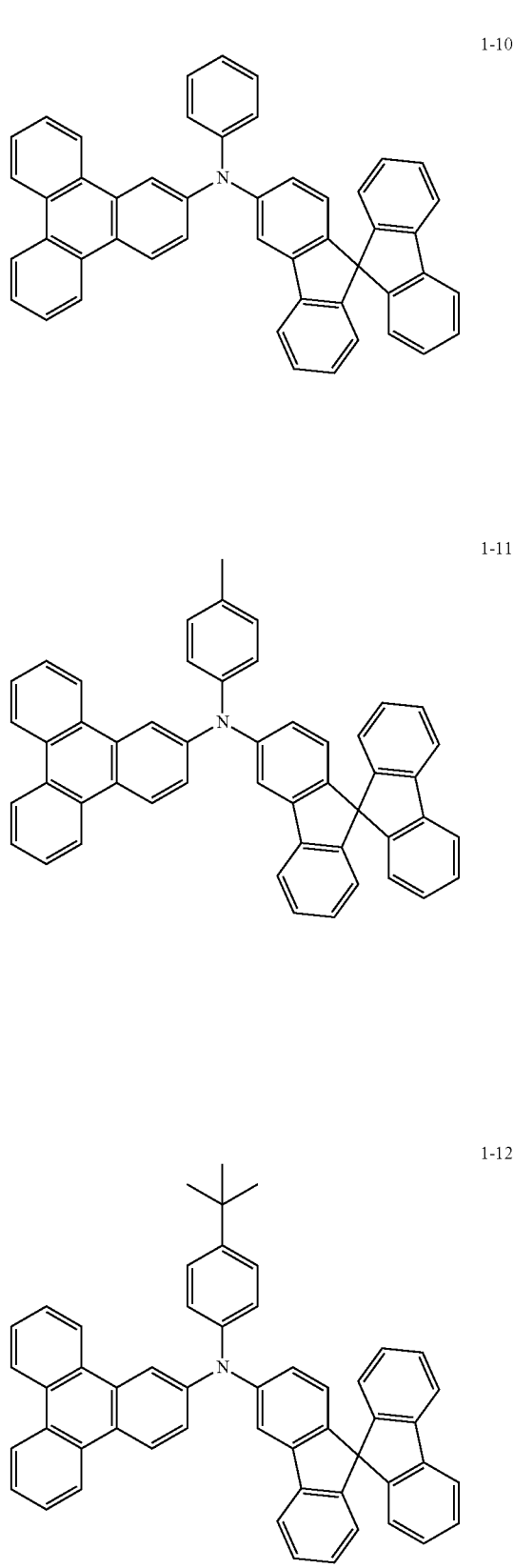

1-13
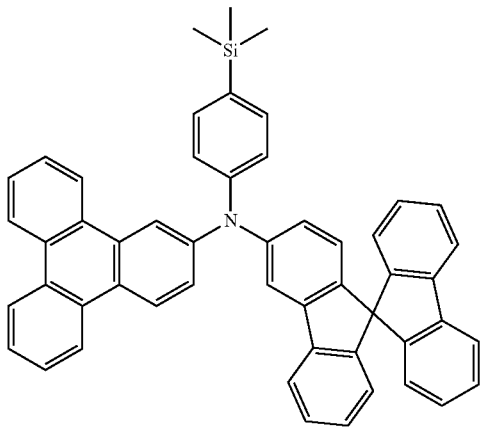
1-17
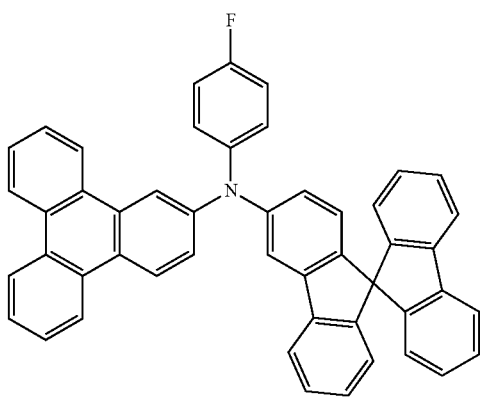
1-14
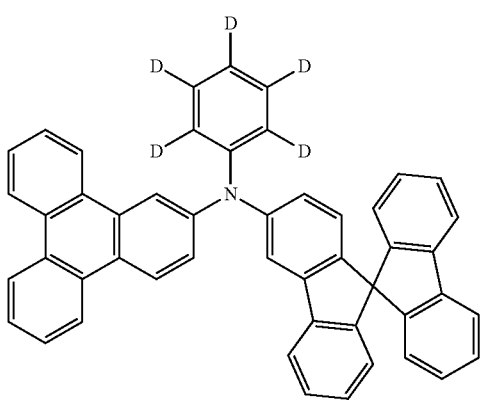
1-18
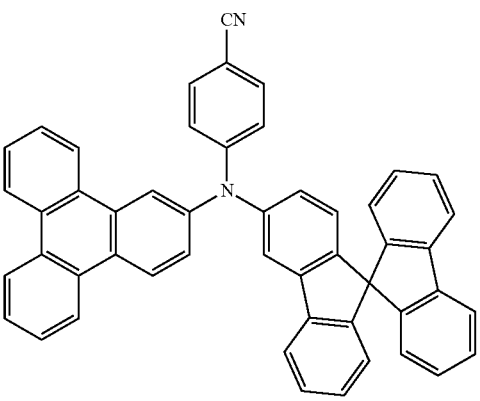
1-15
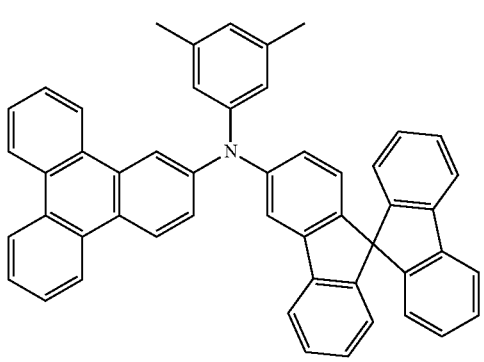
Compounds 1-10 to 1-18 were prepared in the same manner as in the methods of preparing Compounds 1-1 to 1-9, except that a material which is Compound D was used instead of Compound C as a starting material in Preparation Examples 1 to 9.
<Preparation Example 11> Synthesis of the Following Compounds 1-19 to 1-27
1-16
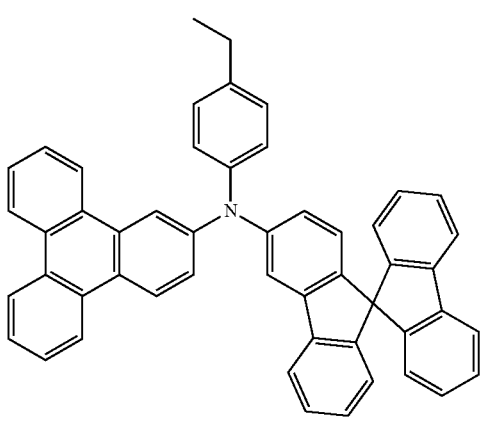
1-19
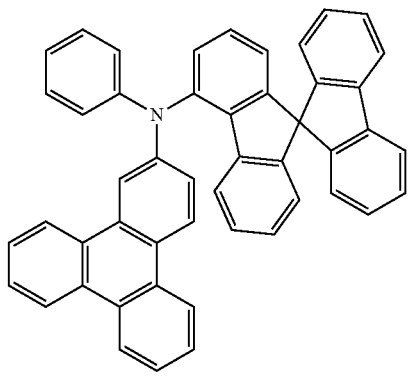

-continued
1-20
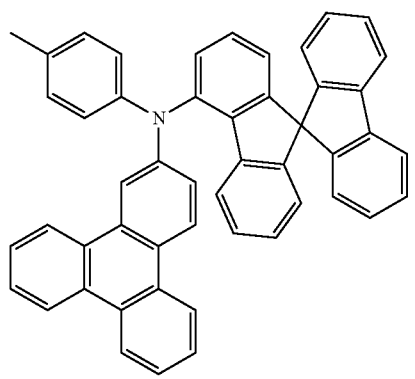
1-21
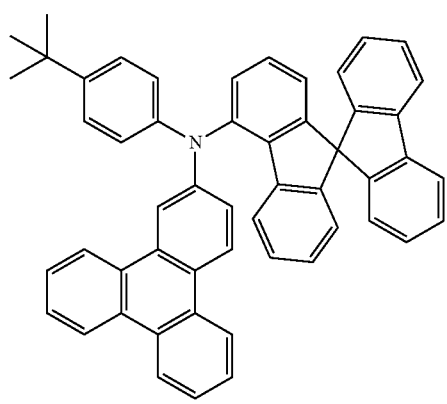
1-22
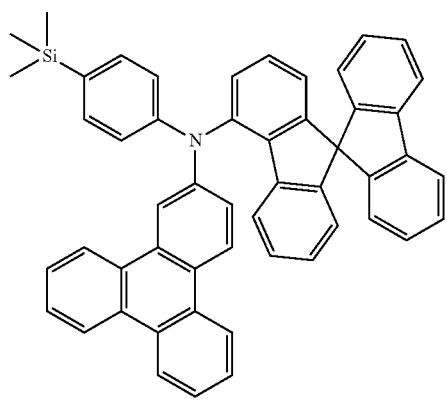
1-23
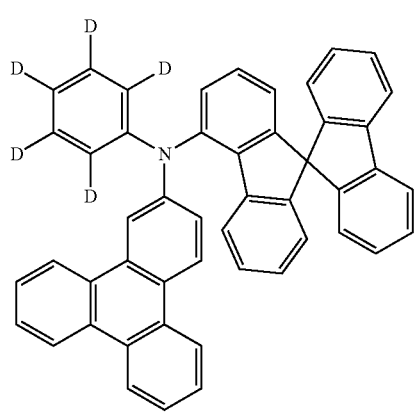
-continued
1-24
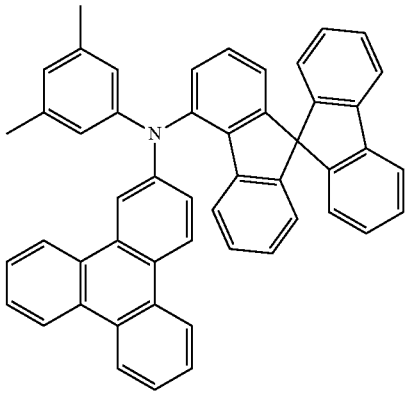
1-25
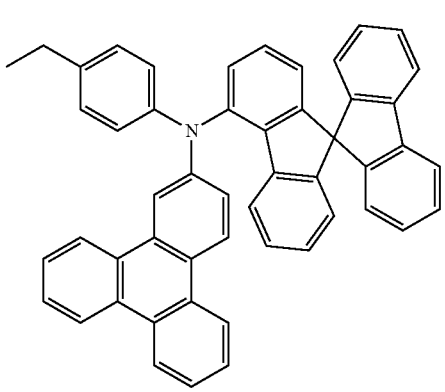
1-26
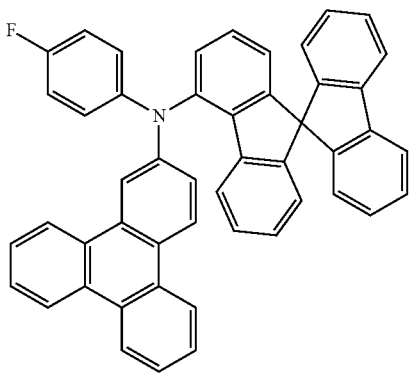
1-27
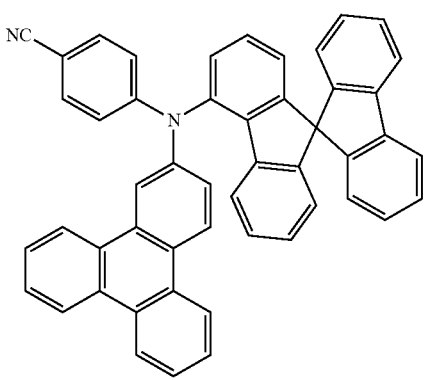

Compounds 1-19 to 1-27 were prepared in the same manner as in the methods of preparing Compounds 1-1 to 1-9, except that a material which is Compound E was used instead of Compound C as a starting material in Preparation Examples 1 to 9.
<Preparation Example 12> Synthesis of the Following Compounds 1-28 to 1-36
1-28
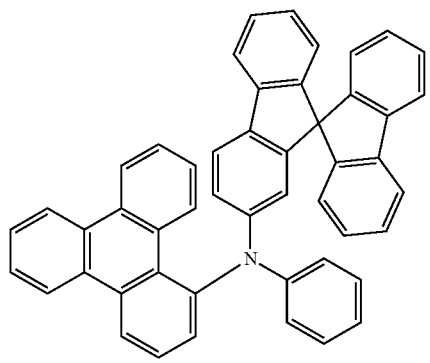
1-29
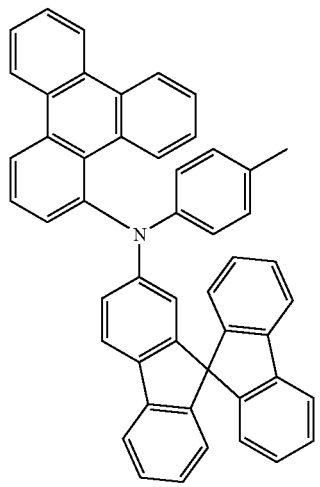
1-30
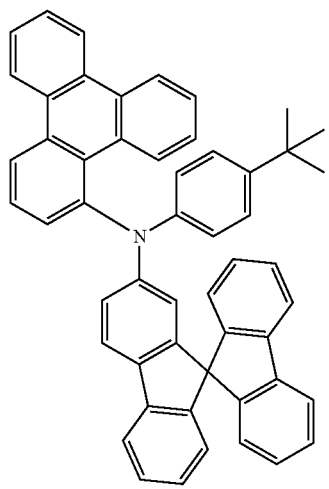
1-31
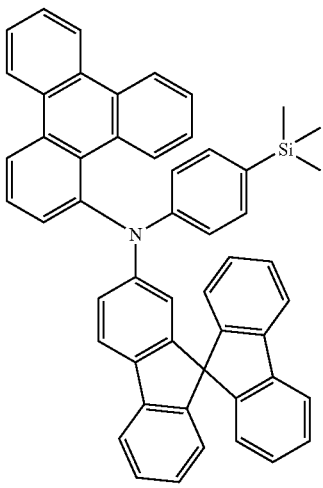
1-32
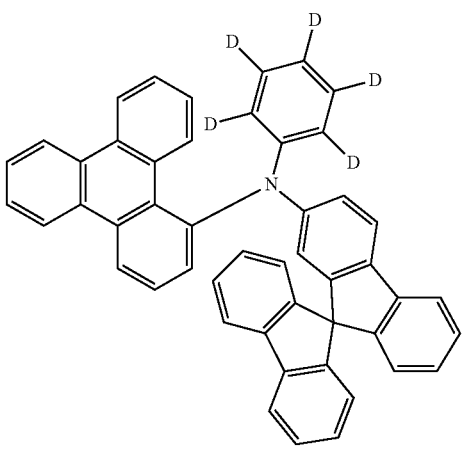
1-33
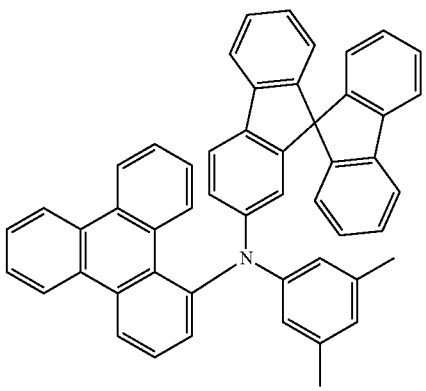

1-34

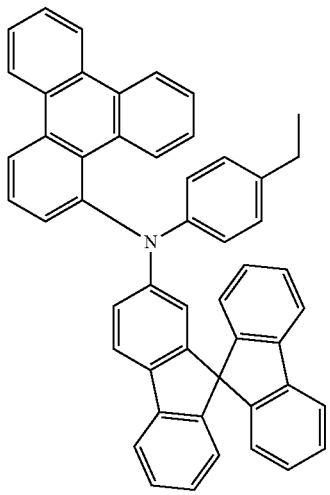

1-35

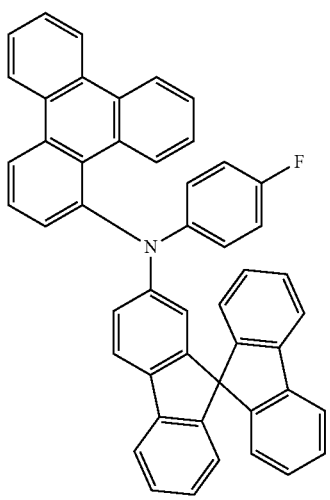

1-36

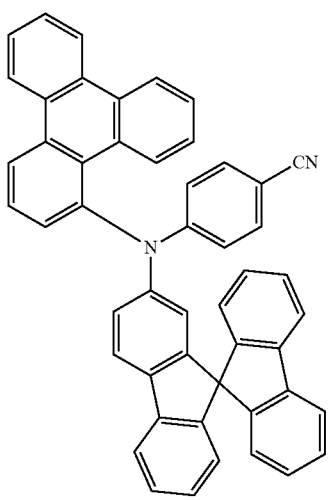

Compounds 1-28 to 1-36 were prepared in the same manner as in the methods of preparing Compounds 1-1 to 1-9, except that a material which is Compound B was used instead of Compound C as a starting material in Preparation Examples 1 to 9.

<Preparation Example 13> Synthesis of the Following Compound 1-37

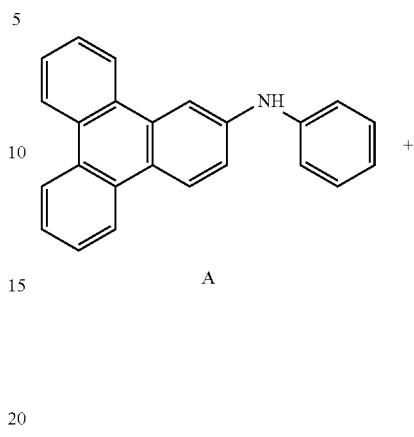

A

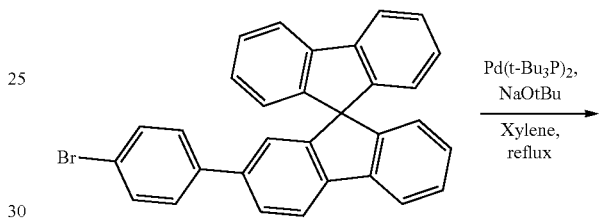

[Compound 1-37]

Under a nitrogen atmosphere, Compound A (10.0 g, 31.35 mmol) and 2-(4-bromophenyl)-9,9'-spirobi[fluorene] (16.21 g, 34.48 mmol) were completely dissolved in 220 ml of xylene in a 500 ml-round bottom flask, and then sodium tert-butoxide (3.92 g, 40.76 mol) was added thereto, bis(tri-tert-butylphosphine) palladium(0) (0.15 g, 0.31 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 310 ml of ethyl acetate to prepare Compound 1-37 (18.54 g, yield: 83%).

MS[M+H]$^+$=710

<Preparation Example 14> Synthesis of the Following Compound 1-38

[Compound 1-38]

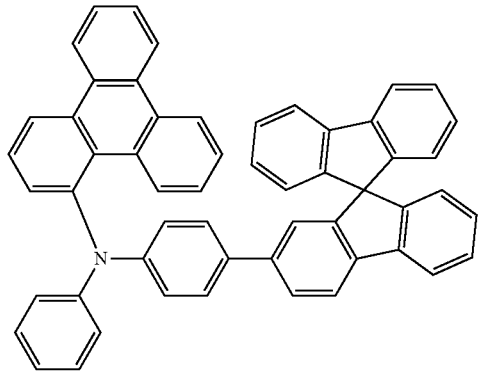

Compound 1-38 was prepared in the same manner as in the method of preparing Compound 1-37, except that a material which is Compound B was used instead of Compound A as a starting material in Preparation Example 13.
MS[M+H]$^+$=710

Experimental Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

[HAT]

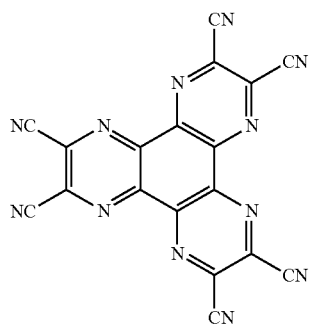

The following compound 4-4'-bis[N-(1-naphthyl)-N-phenylamino]biphenyl (NPB) (300 Å), which is a material for transporting holes, was vacuum deposited on the hole injection layer, thereby forming a hole transport layer.

[NPB]

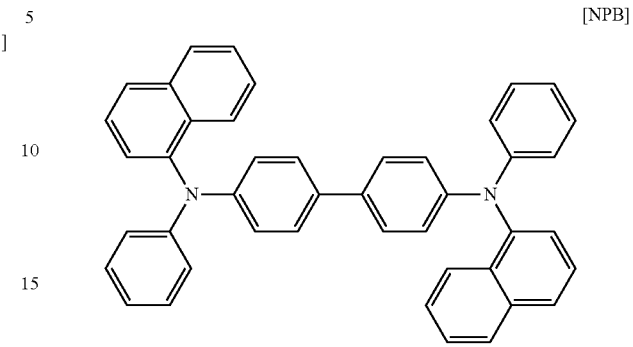

Subsequently, the following Compound 1-1 was vacuum deposited to have a film thickness of 100 Å on the hole transport layer, thereby forming an electron blocking layer.

[Compound 1-1]

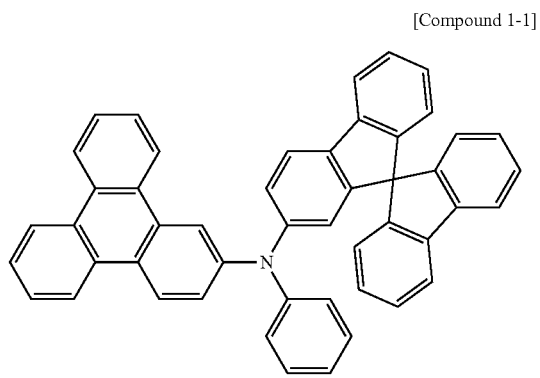 [SMILES: c1ccc(N(c2ccc3c(c2)C2(c4ccccc4-c4ccccc42)c2ccccc2-3)c2ccc3c4ccccc4c4ccccc4c3c2)cc1]

Subsequently, the following BH and BD were vacuum deposited at a weight ratio of 25:1 to have a film thickness of 300 Å on the electron blocking layer, thereby forming a light emitting layer.

[BH]

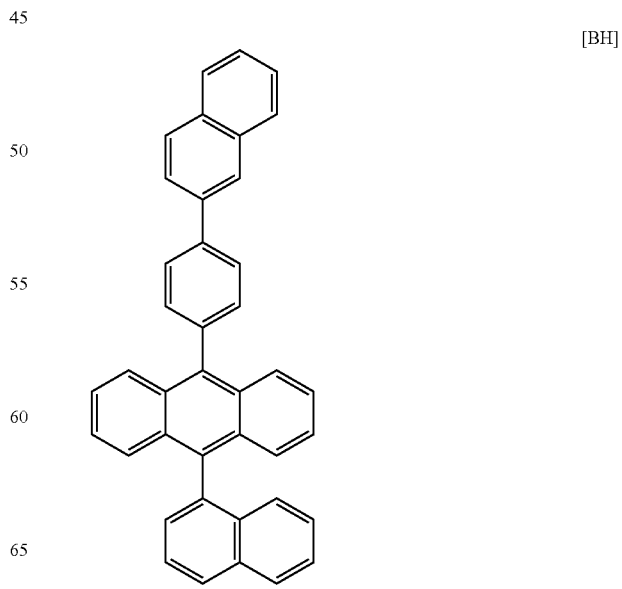

-continued

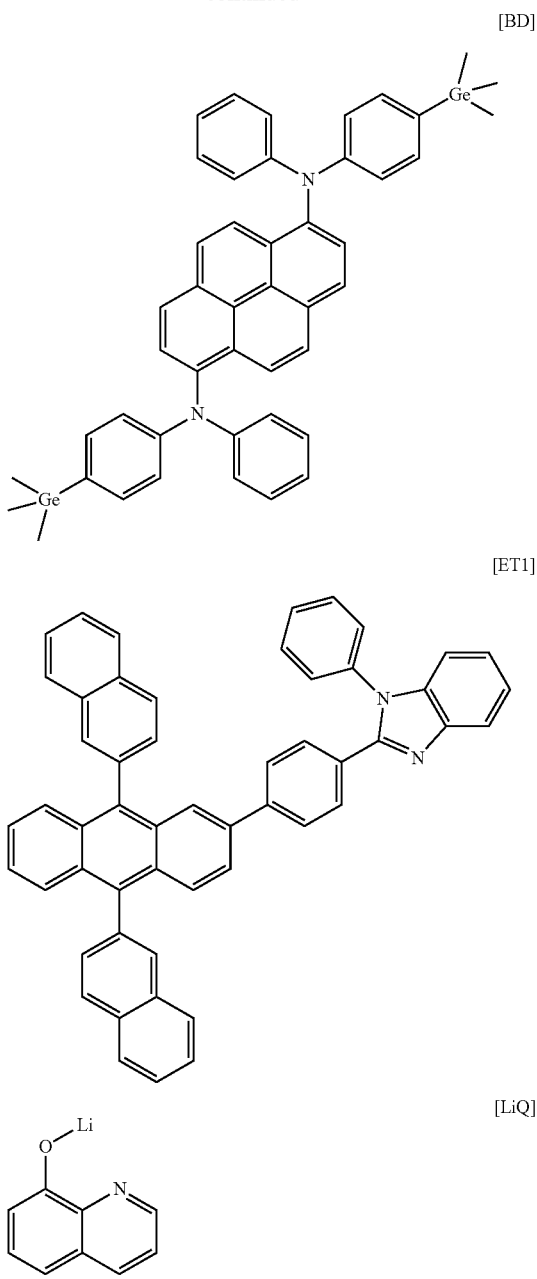

[BD]

[ET1]

[LiQ]

Compound ET1 and Compound LiQ (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

Experimental Example 1-2

An organic light emitting device was manufactured in the same manner as in Experimental Example 1-1, except that Compound 1-2 was used instead of Compound 1-1 in Experimental Example 1-1.

Experimental Example 1-3

An organic light emitting device was manufactured in the same manner as in Experimental Example 1-1, except that Compound 1-3 was used instead of Compound 1-1 in Experimental Example 1-1.

Experimental Example 1-4

An organic light emitting device was manufactured in the same manner as in Experimental Example 1-1, except that Compound 1-4 was used instead of Compound 1-1 in Experimental Example 1-1.

Experimental Example 1-5

An organic light emitting device was manufactured in the same manner as in Experimental Example 1-1, except that Compound 1-5 was used instead of Compound 1-1 in Experimental Example 1-1.

Experimental Example 1-6

An organic light emitting device was manufactured in the same manner as in Experimental Example 1-1, except that Compound 1-6 was used instead of Compound 1-1 in Experimental Example 1-1.

Experimental Example 1-7

An organic light emitting device was manufactured in the same manner as in Experimental Example 1-1, except that Compound 1-7 was used instead of Compound 1-1 in Experimental Example 1-1.

Experimental Example 1-8

An organic light emitting device was manufactured in the same manner as in Experimental Example 1-1, except that Compound 1-10 was used instead of Compound 1-1 in Experimental Example 1-1.

Experimental Example 1-9

An organic light emitting device was manufactured in the same manner as in Experimental Example 1-1, except that Compound 1-19 was used instead of Compound 1-1 in Experimental Example 1-1.

Experimental Example 1-10

An organic light emitting device was manufactured in the same manner as in Experimental Example 1-1, except that Compound 1-28 was used instead of Compound 1-1 in Experimental Example 1-1.

Experimental Example 1-11

An organic light emitting device was manufactured in the same manner as in Experimental Example 1-1, except that Compound 1-37 was used instead of Compound 1-1 in Experimental Example 1-1.

Experimental Example 1-12

An organic light emitting device was manufactured in the same manner as in Experimental Example 1-1, except that Compound 1-38 was used instead of Compound 1-1 in Experimental Example 1-1.

Comparative Example 1-1

An organic light emitting device was manufactured in the same manner as in Experimental Example 1-1, except that EB 1 was used instead of Compound 1-1 in Experimental Example 1-1.

[EB 1]

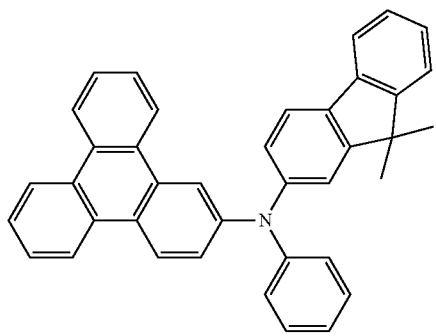

Comparative Example 1-2

An organic light emitting device was manufactured in the same manner as in Experimental Example 1-1, except that the following EB 2 was used instead of Compound 1 in Experimental Example 1-1.

[EB 2]

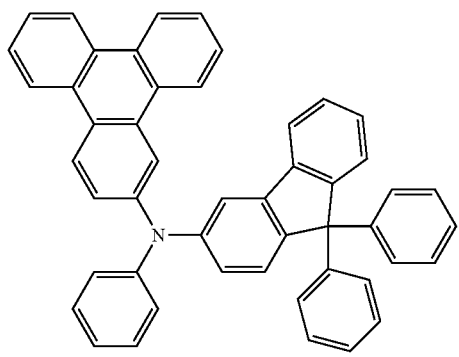

Comparative Example 1-3

An organic light emitting device was manufactured in the same manner as in Experimental Example 1-1, except that the following EB 3 was used instead of Compound 1 in Experimental Example 1-1.

[EB 3]

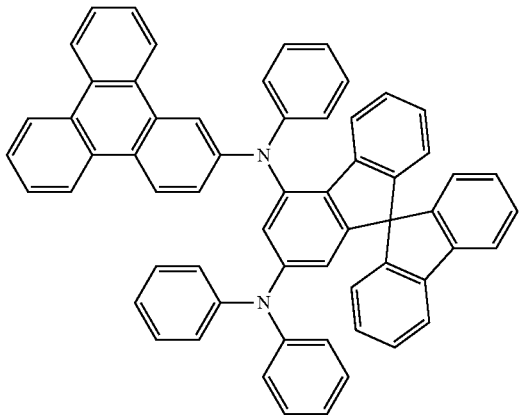

When current was applied to the organic light emitting devices manufactured in Experimental Examples 1-1 to 1-12 and Comparative Examples 1-1 to 1-3, the results of Table 1 were obtained.

TABLE 1

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1-1 | 3.35 | 6.02 | (0.139, 0.125) |
| Experimental Example 1-2 | Compound 1-2 | 3.52 | 5.45 | (0.138, 0.126) |
| Experimental Example 1-3 | Compound 1-3 | 3.57 | 5.76 | (0.138, 0.127) |
| Experimental Example 1-4 | Compound 1-4 | 3.68 | 5.70 | (0.137, 0.125) |
| Experimental Example 1-5 | Compound 1-5 | 3.69 | 5.68 | (0.136, 0.125) |
| Experimental Example 1-6 | Compound 1-6 | 3.64 | 5.72 | (0.136, 0.127) |
| Experimental Example 1-7 | Compound 1-7 | 3.63 | 5.70 | (0.136, 0.125) |
| Experimental Example 1-8 | Compound 1-10 | 3.41 | 5.88 | (0.137, 0.125) |
| Experimental Example 1-9 | Compound 1-19 | 3.40 | 5.89 | (0.138, 0.125) |
| Experimental Example 1-10 | Compound 1-28 | 3.38 | 5.98 | (0.136, 0.125) |
| Experimental Example 1-11 | Compound 1-37 | 3.43 | 5.91 | (0.137, 0.125) |
| Experimental Example 1-12 | Compound 1-38 | 3.42 | 5.91 | (0.136, 0.125) |
| Comparative Example 1-1 | EB 1 | 4.46 | 4.72 | (0.138, 0.127) |
| Comparative Example 1-2 | EB 2 | 4.35 | 4.88 | (0.139, 0.125) |
| Comparative Example 1-3 | EB 3 | 4.52 | 4.68 | (0.139, 0.125) |

As shown in Table 1, it can be seen that the compounds of Experimental Examples 1-1 to 1-12 were used as the electron blocking layer in the organic light emitting device, and exhibit lower voltage and higher efficiency characteristics than the organic light emitting devices of Comparative Example 1-1 in which the compound of the present invention was substituted with an alkyl group instead of spirobifluorene, Comparative Example 1-2 in which the compound of the present invention was substituted with an aryl group instead of spirobifluorene, and Comparative Example 1-3 in which two arylamine groups were substituted.

It could be confirmed that the compound derivatives of the Chemical Formulae according to the present invention have an excellent electron suppressing capability, and thus exhibit low voltage and high efficiency characteristics, and may be applied to the electron blocking layer of the organic light emitting device.

Experimental Example 2

<Experimental Example 2-1> to <Experimental Example 2-12>

An experiment was performed in the same manner as in Experimental Example 1, except that TCTA was used as the electron blocking layer, and the compounds in Experimental Examples 1-1 to 1-12 were used instead of NPB as the hole transport layer.

Comparative Example 2-1

An experiment was performed in the same manner as in Experimental Example 2, except that TCTA was used as the electron blocking layer, and HT 1 was used as the hole transport layer.

[HT 1]

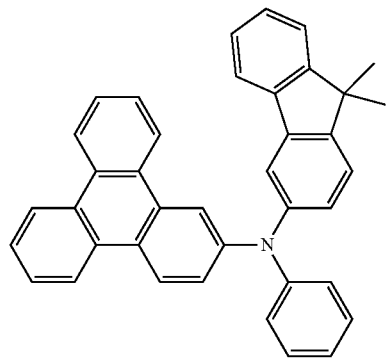

Comparative Example 2-2

An experiment was performed in the same manner as in Experimental Example 2, except that TCTA was used as the electron blocking layer, and HT 2 was used as the hole transport layer.

[HT 2]

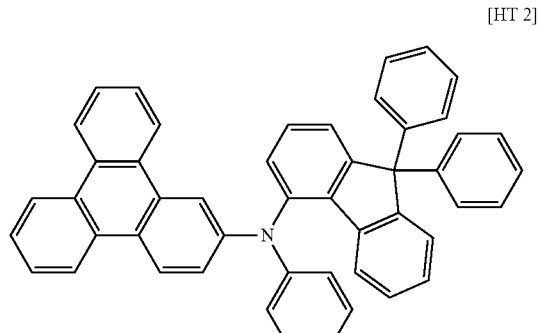

Comparative Example 2-3

An experiment was performed in the same manner as in Experimental Example 2, except that TCTA was used as the electron blocking layer, and HT 3 was used as the hole transport layer.

[HT 3]

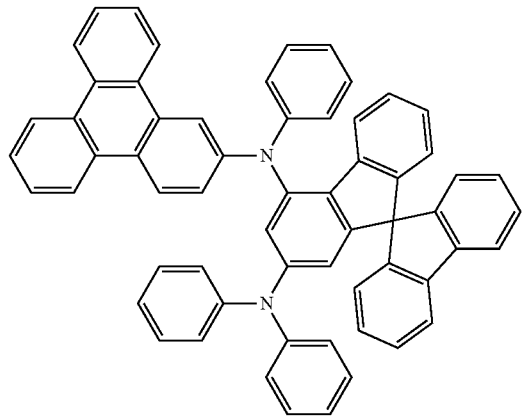

When current was applied to the organic light emitting devices manufactured in Experimental Examples 2-1 to 2-12 and Comparative Examples 2-1 to 2-3, the results of Table 2 were obtained.

TABLE 2

| | Compound (Hole transport layer) | Voltage (V@10 mA/cm$^2$) | Efficiency (cd/A@10 mA/cm$^2$) | Color coordinate (x, y) |
| --- | --- | --- | --- | --- |
| Experimental Example 2-1 | Compound 1-1 | 3.75 | 5.95 | (0.139, 0.126) |
| Experimental Example 2-2 | Compound 1-2 | 3.72 | 5.98 | (0.138, 0.126) |
| Experimental Example 2-3 | Compound 1-3 | 3.87 | 5.85 | (0.138, 0.127) |
| Experimental Example 2-4 | Compound 1-4 | 3.88 | 5.84 | (0.137, 0.125) |
| Experimental Example 2-5 | Compound 1-5 | 3.89 | 5.82 | (0.136, 0.125) |
| Experimental Example 2-6 | Compound 1-6 | 3.84 | 5.83 | (0.136, 0.127) |
| Experimental Example 2-7 | Compound 1-7 | 3.83 | 5.80 | (0.136, 0.125) |
| Experimental Example 2-8 | Compound 1-10 | 3.84 | 5.81 | (0.137, 0.125) |
| Experimental Example 2-9 | Compound 1-19 | 3.93 | 5.71 | (0.138, 0.125) |
| Experimental Example 2-10 | Compound 1-28 | 3.98 | 5.72 | (0.136, 0.125) |
| Experimental Example 2-11 | Compound 1-37 | 3.93 | 5.75 | (0.137, 0.125) |
| Experimental Example 2-12 | Compound 1-38 | 3.95 | 5.75 | (0.136, 0.125) |
| Comparative Example 2-1 | HT 1 | 4.55 | 4.83 | (0.138, 0.127) |
| Comparative Example 2-2 | HT 2 | 4.63 | 4.75 | (0.139, 0.125) |
| Comparative Example 2-3 | HT 3 | 4.44 | 4.94 | (0.139, 0.126) |

As shown in Table 2, it can be seen that the compounds of Experimental Examples 2-1 to 2-12 were used as the hole transport layer in the organic light emitting device, and exhibit lower voltage and higher efficiency characteristics than the organic light emitting devices of Comparative Example 2-1 in which the compound of the present invention was substituted with an alkyl group instead of spirobifluorene, Comparative Example 2-2 in which the compound of the present invention was substituted with an aryl group instead of spirobifluorene, and Comparative Example 2-3 in which two arylamine groups were substituted.

It could be confirmed that the compound derivatives of the Chemical Formulae according to the present invention also have an excellent hole transporting capability, and thus exhibit low voltage and high efficiency characteristics, and may be applied to the hole transport layer of the organic light emitting device.

Although the preferred exemplary embodiments (an electron blocking layer and a hole transport layer) of the present invention have been described above, the present invention is not limited thereto, and various modifications can be made and carried out within the scope of the claims and the detailed description of the invention, and also fall within the scope of the invention.

EXPLANATION OF REFERENCE NUMERALS AND SYMBOLS

1: Substrate
2: Positive electrode
3: Light emitting layer
4: Negative electrode
5: Hole injection layer
6: Hole transport layer
7: Light emitting layer
8: Electron transport layer

The invention claimed is:

1. A compound represented by any one of the following Chemical Formulae 4 to 6:

[Chemical Formula 4]

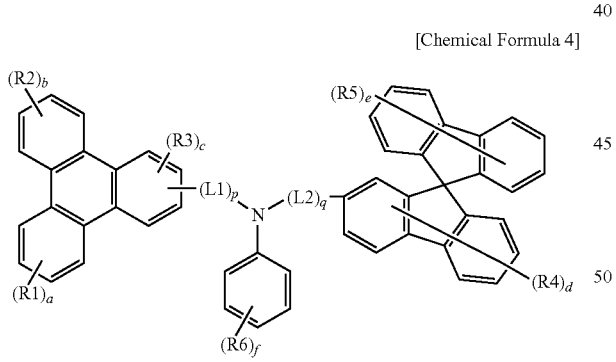

[Chemical Formula 5]

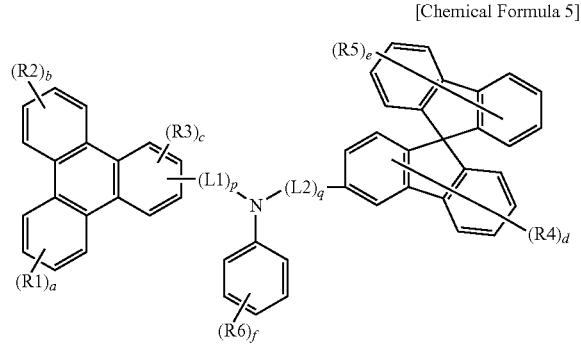

[Chemical Formula 6]

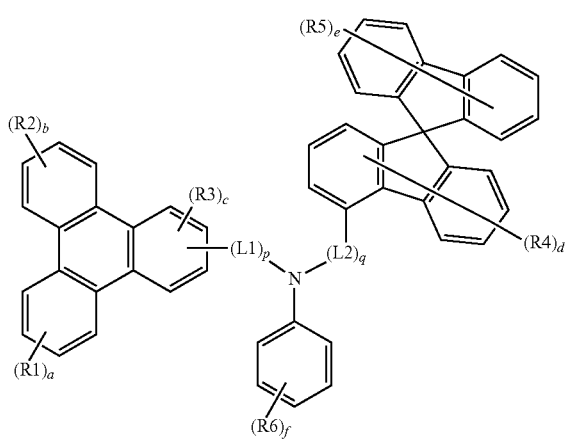

in Chemical Formulae 4 to 6,
L1 and L2 are a direct bond,
R1 to R5 are hydrogen,
the

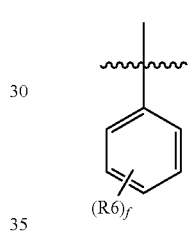

moiety is represented by any one selected from the following structures:

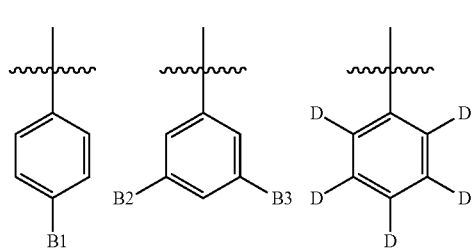

wherein B1 is deuterium; a halogen group; a nitrile group; an alkyl group having 1 to 6 carbon atoms; or a silyl group substituted with an alkyl group having 1 to 6 carbon atoms, B2 and B3 are the same as or different from each other and are each independently an alkyl group having 1 to 6 carbon atoms, a and b are an integer of 4,
c is an integer of 3,
d is an integer of 7,
e is an integer of 8,
f is an integer of 1, 2 or 5, and
p and q are an integer of 1.

2. The compound of claim 1, which is represented by any one of the following Chemical Formulae 7 to 9:

[Chemical Formula 7]

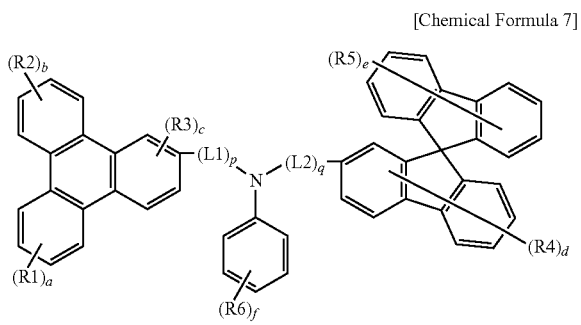

[Chemical Formula 8]

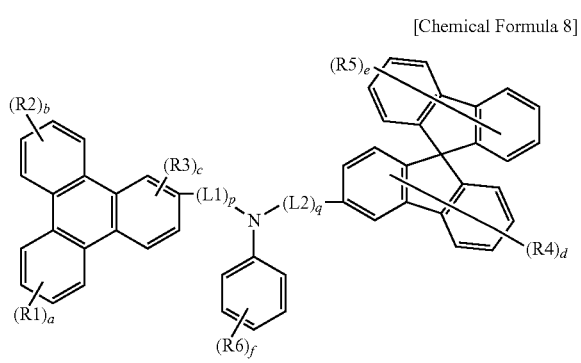

[Chemical Formula 9]

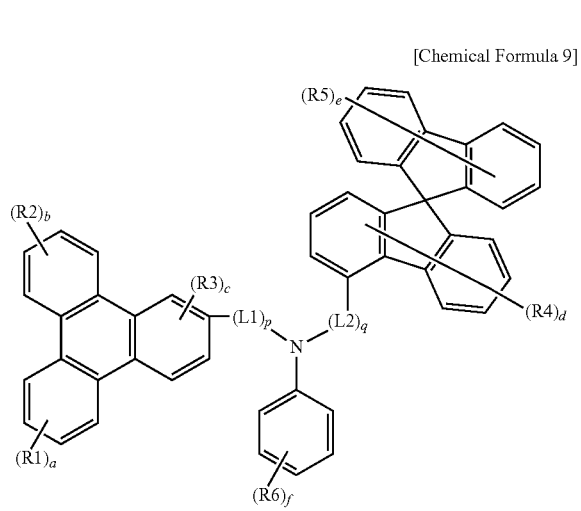

in Chemical Formulae 7 to 9, definitions of L1, L2, R1 to R6, p, q, a, b, c, d, e, and f are the same as those in Chemical Formulae 4-6.

3. The compound of claim 1, which is represented by any one of the following Chemical Formulae 10 to 12:

[Chemical Formula 10]

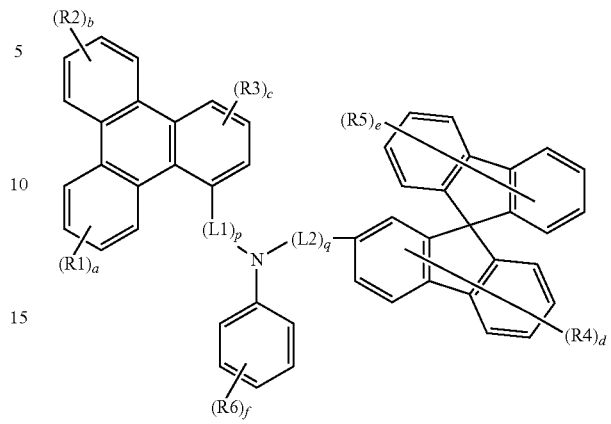

[Chemical Formula 11]

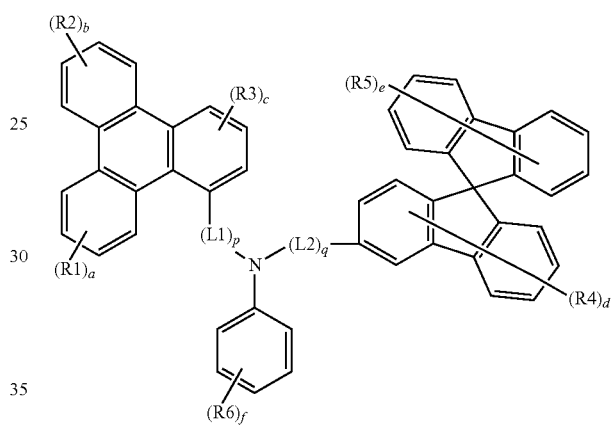

[Chemical Formula 12]

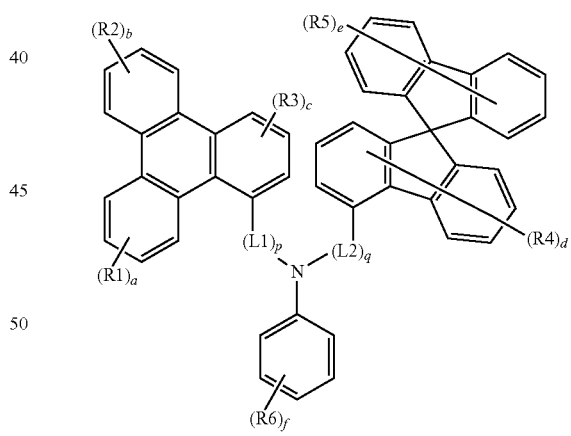

in Chemical Formulae 10 to 12, definitions of L1, L2, R1 to R6, p, q, a, b, c, d, e, and f are the same as those in Chemical Formulas 4-6.

4. The compound of claim 1, wherein B1 is an alkyl group having 1 to 5 carbon atoms; or a silyl group substituted with an alkyl group having 1 to 5 carbon atoms, and B2 to B3 are the same as or different from each other and are each independently an alkyl group having 1 to 5 carbon atoms.

5. The compound of claim 1, which is any one selected from the following compounds:

-continued
7
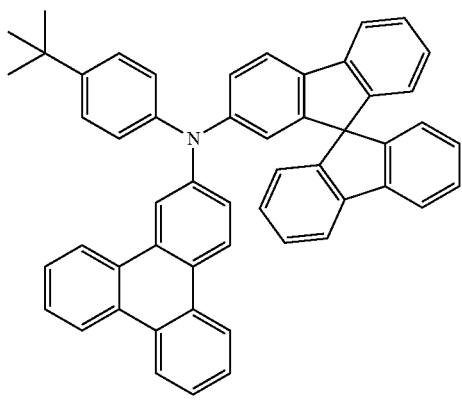
8
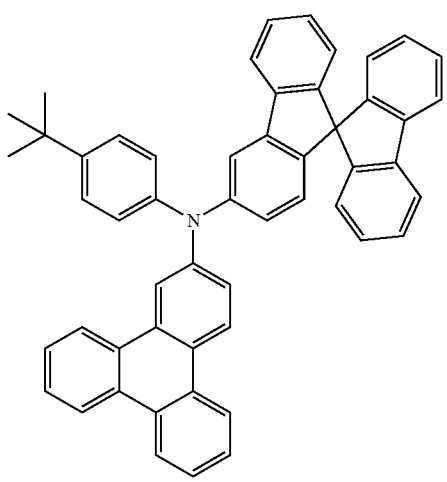
9
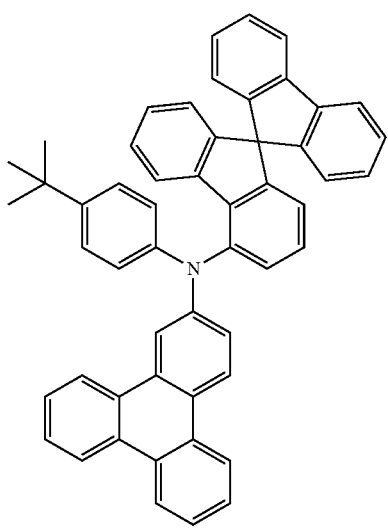
10
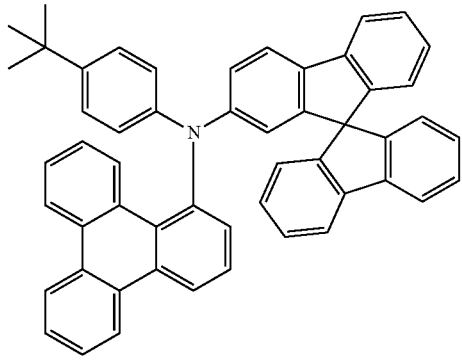
11
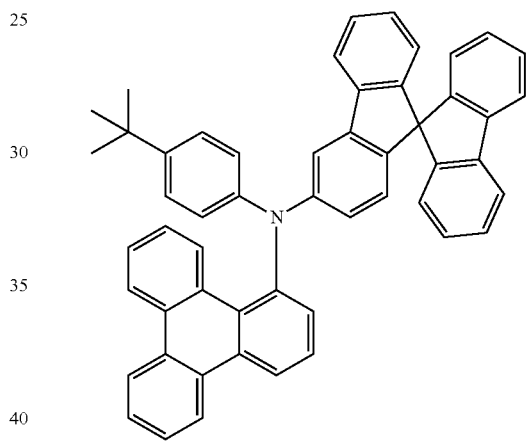
12
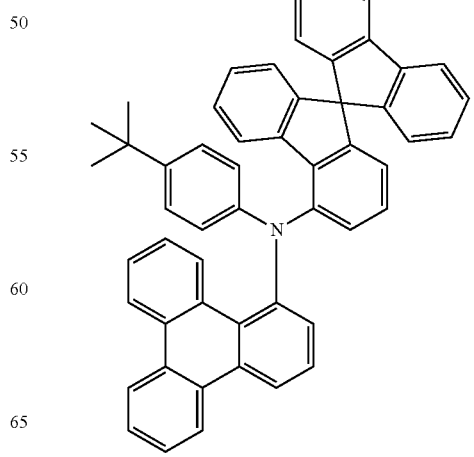

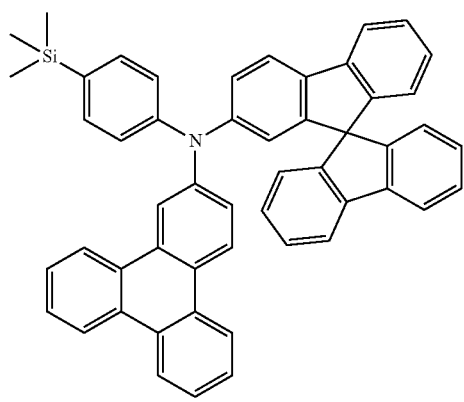
13
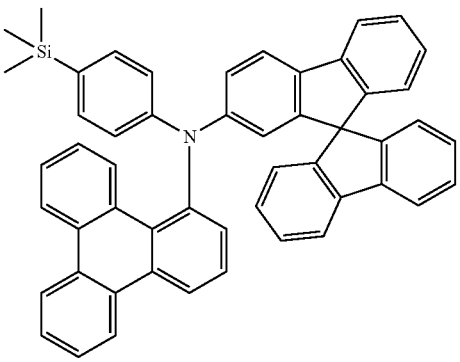
16
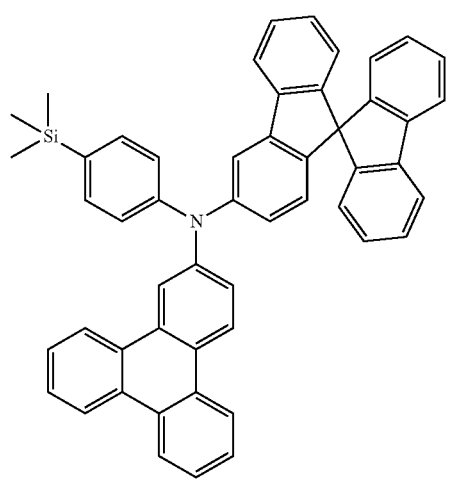
14
17
15
18
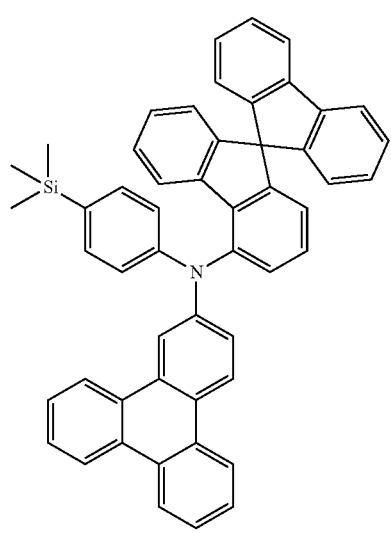

19
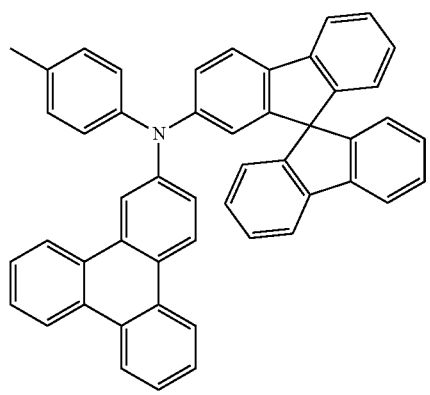
20
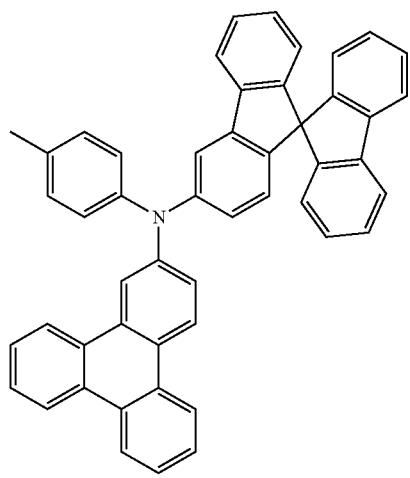
21
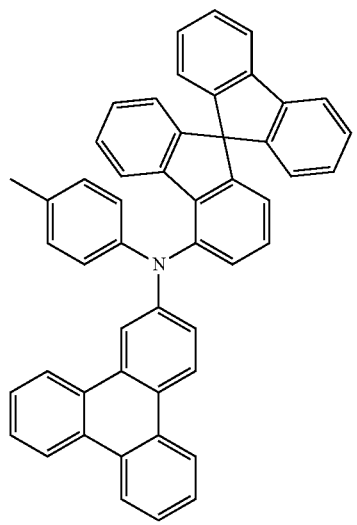
22
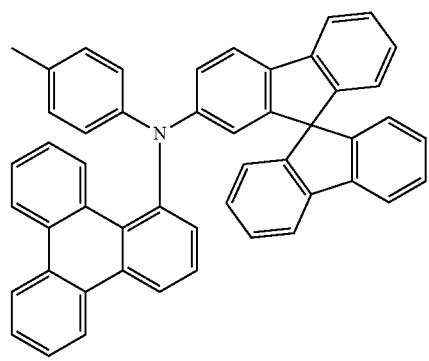
23
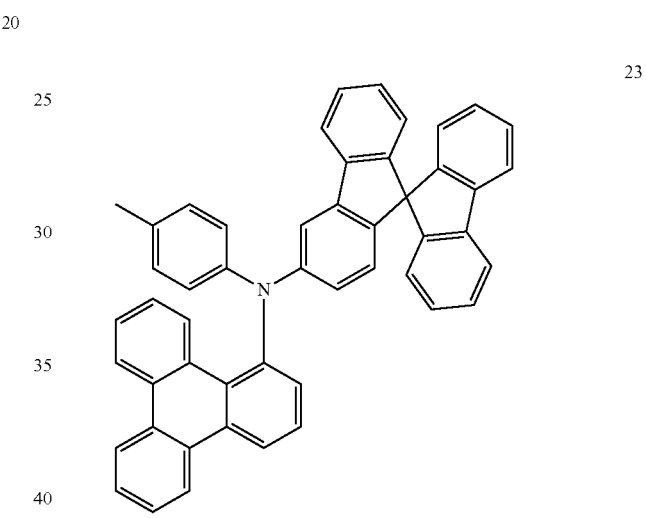
24
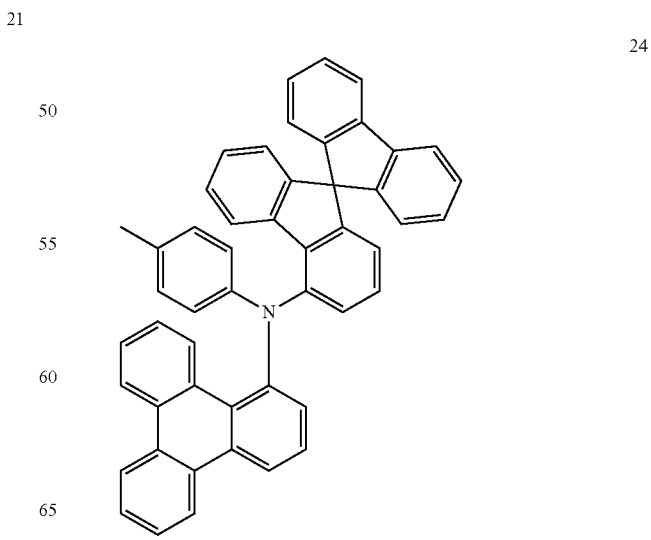

85
-continued
25
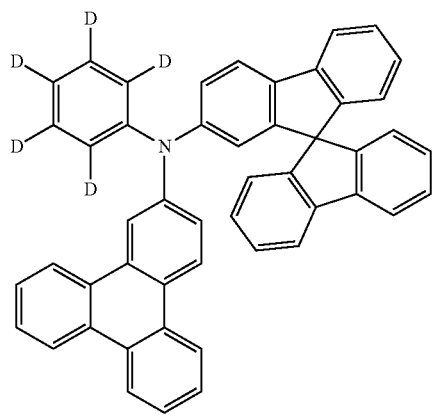
26
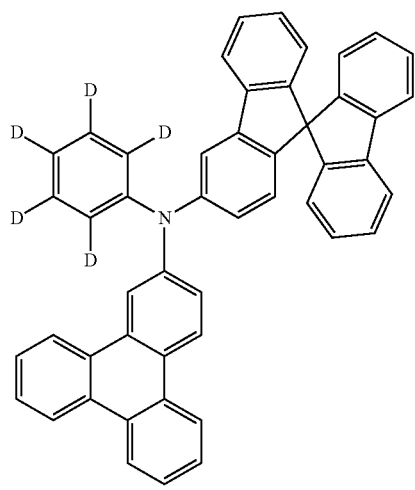
27
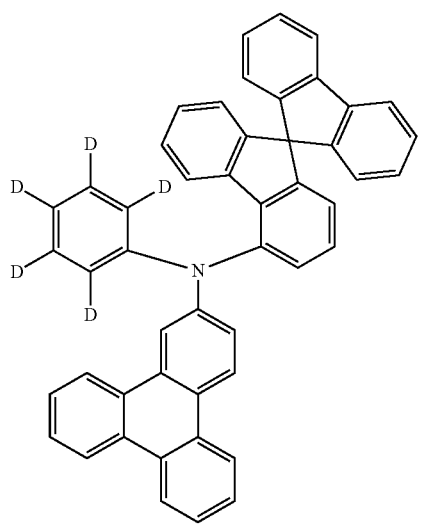
86
-continued
28
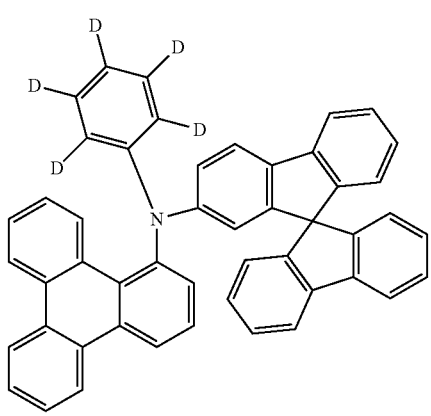
29
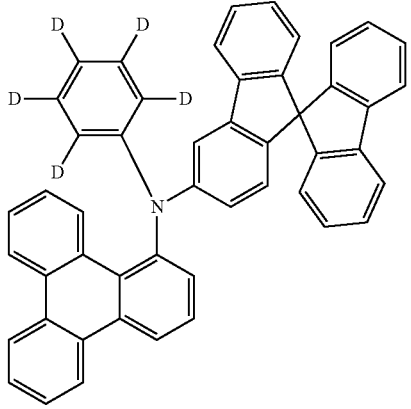
30
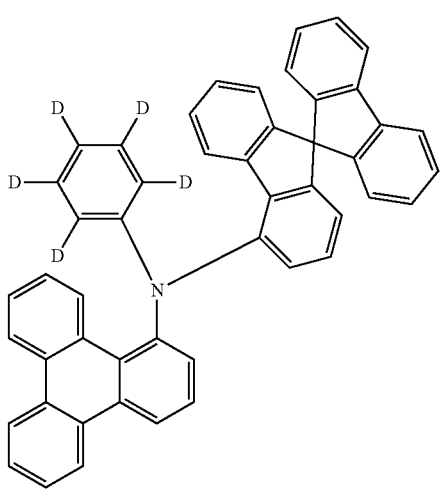

31
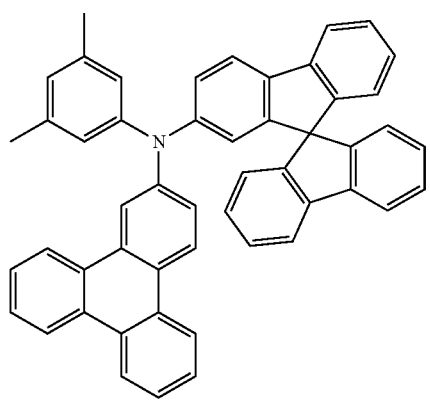
32
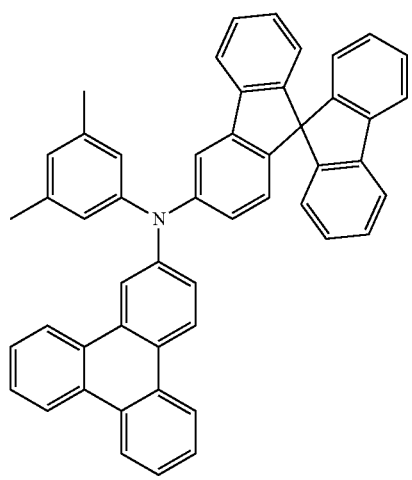
33
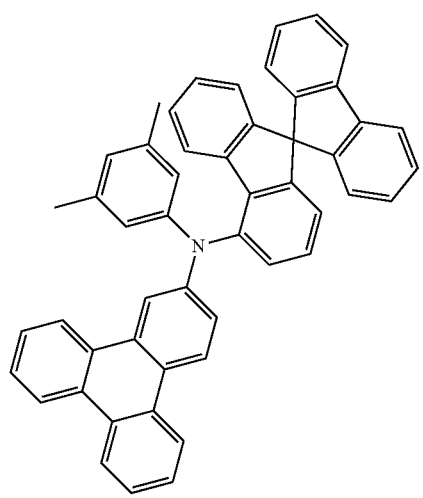
34
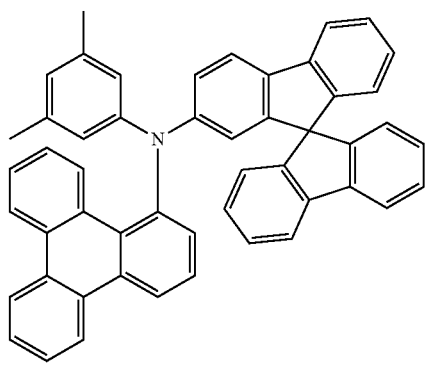
35
36

49
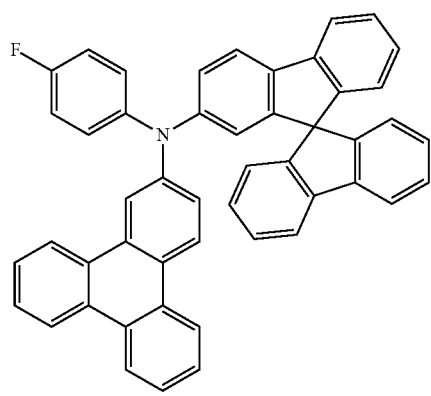
50
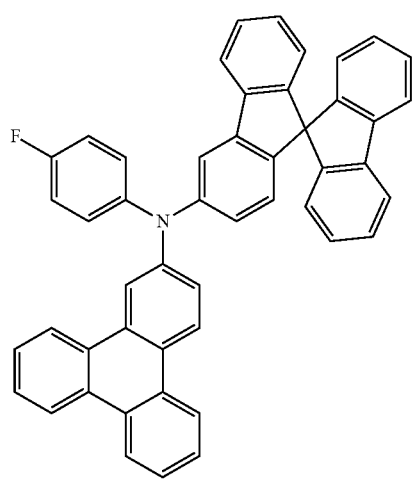
51
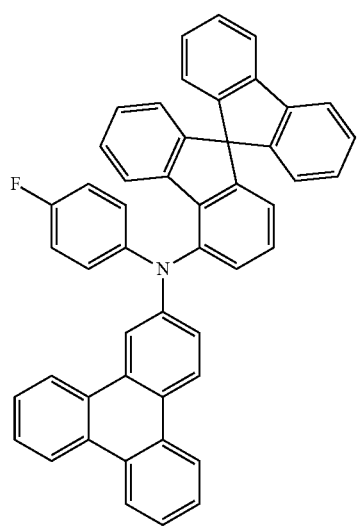
52
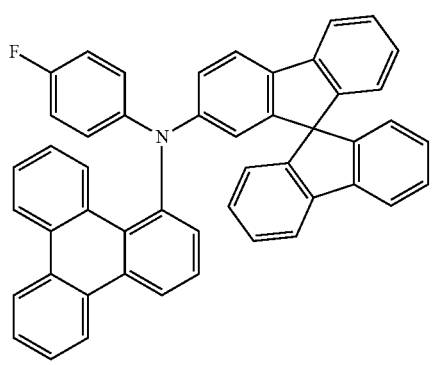
53
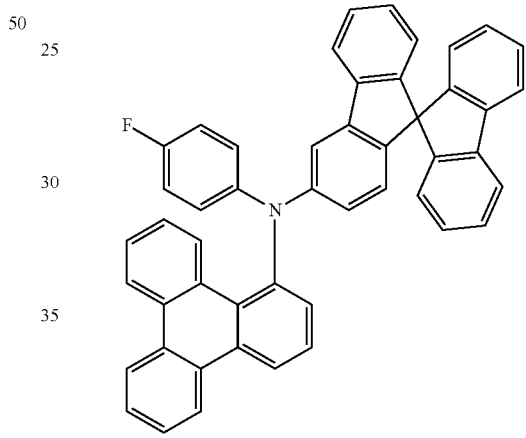
54
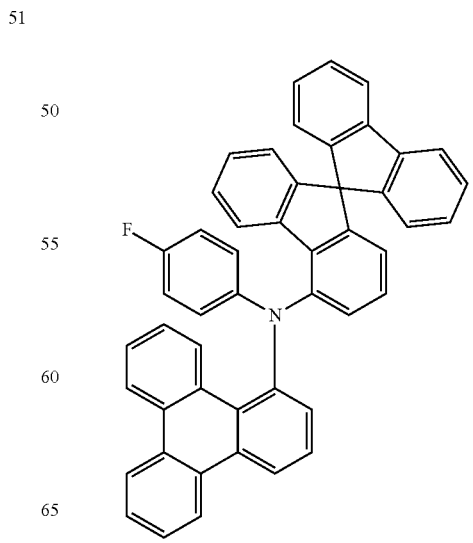

-continued

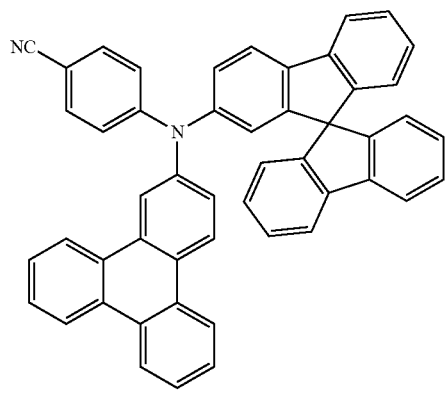
55

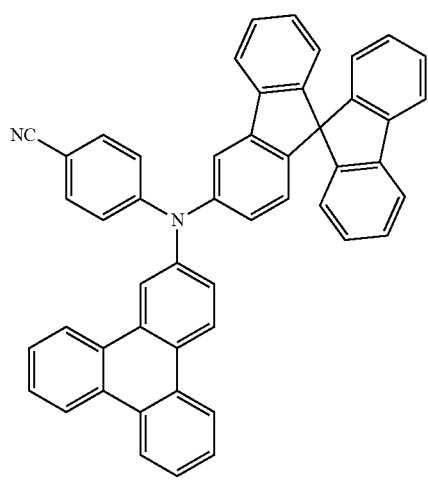
56

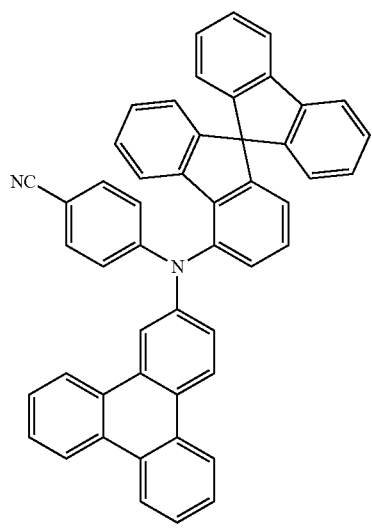
57

-continued

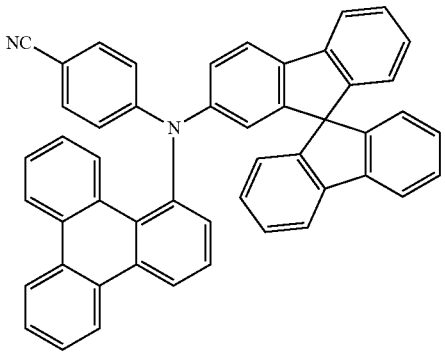
58

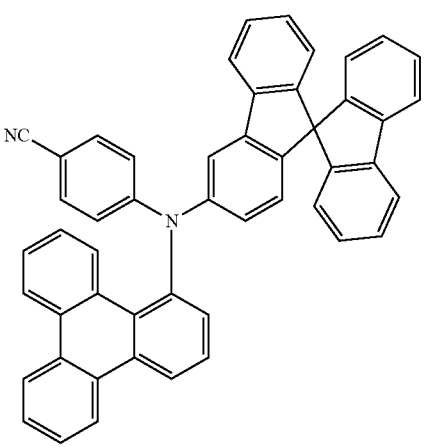
59

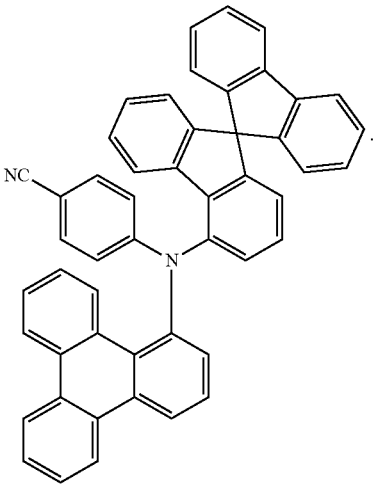
60

6. An organic light emitting device comprising:
a first electrode;
a second electrode provided to face the first electrode; and
at least one organic material layer provided between the first electrode and the second electrode,
wherein the at least one organic material layer comprises the compound of claim 1.

7. The organic light emitting device of claim 6, wherein the at least one organic material layer comprising the compound is a hole injection layer; a hole transport layer; an electron blocking layer; or a layer which simultaneously injects and transports holes.

8. The organic light emitting device of claim 6, wherein the at least one organic material layer comprising the compound is an electron injection layer; an electron transport layer; or a layer which simultaneously injects and transports electrons.

9. The organic light emitting device of claim 6, wherein the at least one organic material layer comprising the compound is a light emitting layer.

10. The organic light emitting device of claim 6, wherein the at least one organic material layer comprises a light emitting layer, and the light emitting layer comprises a compound represented by the following Chemical Formula 1-A:

[Chemical Formula 1-A]

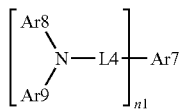

in Chemical Formula 1-A,
n1 is an integer of 1 or more,
Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L4 is a direct bond; a substituted or unsubstituted arylene group; or a substituted or unsubstituted heteroarylene group,
Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and
when n1 is 2 or more, two or more structures in the parenthesis are the same as or different from each other.

11. The organic light emitting device of claim 10, wherein L4 is a direct bond, Ar7 is a divalent pyrene group, Ar8 and Ar9 are the same as or different from each other, and are each independently an aryl group which is unsubstituted or substituted with a germanium group substituted with an alkyl group, and n1 is 2.

12. The organic light emitting device of claim 6, wherein the at least one organic material layer comprises a light emitting layer, and the light emitting layer comprises a compound represented by the following Chemical Formula 2-A:

[Chemical Formula 2-A]

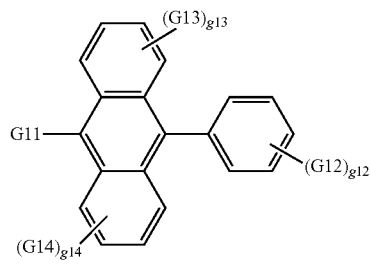

in Chemical Formula 2-A,
G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

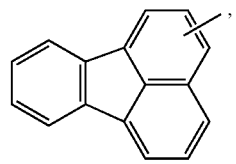

G12 is a phenyl group, a 1-naphtyl group, a 2-naphtyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4-methylbiphenylyl group, a 4"-t-butyl-p-terphenyl-4-yl group, or a 3-fluoranthenyl group,
G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group,
g12 is an integer of 1 to 5,
g13 and g14 are each an integer of 1 to 4, and
when g12 to g14 are each 2 or more, two or more structures in the parenthesis are the same as or different from each other.

13. The organic light emitting device of claim 12, wherein G11 is a 1-naphthyl group, and G12 is a 2-naphthyl group.

14. The organic light emitting device of claim 10, wherein the at least one light emitting layer comprises a compound represented by the following Chemical Formula 2-A:

[Chemical Formula 2-A]

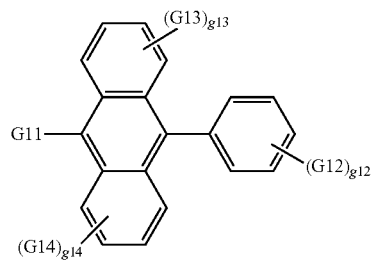

in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

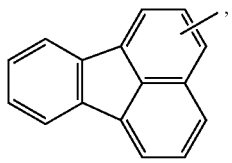

G12 is a phenyl group, a 1-naphtyl group, a 2-naphtyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

* * * * *